(12) United States Patent
Guthrie et al.

(10) Patent No.: US 9,581,530 B2
(45) Date of Patent: Feb. 28, 2017

(54) MULTICHANNEL IMPACT RESPONSE FOR MATERIAL CHARACTERIZATION

(71) Applicant: BRIGHAM YOUNG UNIVERSITY, Provo, UT (US)

(72) Inventors: William S. Guthrie, Provo, UT (US); Brian Mazzeo, Provo, UT (US); Jacob Larsen, Katsville, UT (US); Joseph McElderry, Jacksonville, AR (US)

(73) Assignee: Brigham Young University, Provo, UT (US)

( * ) Notice: Subject to any disclaimer, the term of this patent is extended or adjusted under 35 U.S.C. 154(b) by 0 days.

(21) Appl. No.: 14/795,889

(22) Filed: Jul. 9, 2015

(65) Prior Publication Data

US 2016/0011088 A1    Jan. 14, 2016

Related U.S. Application Data

(60) Provisional application No. 62/022,489, filed on Jul. 9, 2014, provisional application No. 62/115,144, filed
(Continued)

(51) Int. Cl.
| | |
|---|---|
| *G01M 7/00* | (2006.01) |
| *G01N 3/06* | (2006.01) |
| *G01N 3/34* | (2006.01) |
| *G01N 3/48* | (2006.01) |
| *G01N 29/04* | (2006.01) |

(Continued)

(52) U.S. Cl.
CPC ............... *G01N 3/06* (2013.01); *G01N 3/34* (2013.01); *G01N 3/48* (2013.01); *G01N 29/045* (2013.01); *G01N 29/38* (2013.01); *G01N 29/42* (2013.01); *G01N 2291/0232* (2013.01); *G01N 2291/0427* (2013.01)

(58) Field of Classification Search
CPC ...... G01N 3/303; G01N 3/30; G01N 3/06; G01N 7/08
USPC ................. 73/12.13, 12.09, 12.01
See application file for complete search history.

(56) References Cited

U.S. PATENT DOCUMENTS

| | | | | |
|---|---|---|---|---|
| 4,285,243 A | * | 8/1981 | Collingwood ....... | G01N 29/265 73/623 |
| 6,536,553 B1 | * | 3/2003 | Scanlon ............... | G01N 29/069 181/108 |

(Continued)

OTHER PUBLICATIONS

I. Bork, "Measuring the acoustical properties of mallets," Applied Acoustics, vol. 30, pp. 207-218, // 1990.

(Continued)

*Primary Examiner* — Lisa Caputo
*Assistant Examiner* — Nigel Plumb
(74) *Attorney, Agent, or Firm* — Brake Hughes Bellermann LLP

(57) ABSTRACT

A non-destructive test system includes a plurality of impact devices including a knob configured to generate at least one flexural mode in a material when a surface of the material is impacted by the knob, a controller configured to independently control each of the plurality of impact devices, the controller having a communications channel for each of the plurality of impact devices, and a microphone configured to detect an acoustic response generated upon impact of the knob on the surface of the material, the acoustic response being based on the at least one flexural modes generated in the material.

20 Claims, 17 Drawing Sheets

Related U.S. Application Data on Feb. 11, 2015, provisional application No. 62/162,413, filed on May 15, 2015.

(51) Int. Cl.
*G01N 29/38* (2006.01)
*G01N 29/42* (2006.01)

(56) References Cited

U.S. PATENT DOCUMENTS

| | | | | |
|---|---|---|---|---|
| 6,581,466 | B1* | 6/2003 | Costley | G01N 29/045 |
| | | | | 73/584 |
| 2007/0017297 | A1* | 1/2007 | Georgeson | G01M 5/0016 |
| | | | | 73/801 |
| 2011/0154902 | A1* | 6/2011 | Fisk | G01N 29/265 |
| | | | | 73/592 |
| 2013/0325308 | A1* | 12/2013 | Friedlander | B60W 40/06 |
| | | | | 701/117 |

OTHER PUBLICATIONS

N. Gucunski, A. Imani, F. Romero, S. Nazarian, D. Yuan, H. Wiggenhauser, et al., Nondestructive testing to identify concrete bridge deck deterioration. Washington, D.C. : Transportation Research Board, 2013.

T. Oh, J. S. Popovics, and S.-H. Sim, "Analysis of vibration for regions above rectangular delamination defects in solids," Journal of Sound and Vibration, vol. 332, pp. 1766-1776, Apr. 1, 2013.

M. Sansalone, "Impact-echo: The complete story," ACI Structural Journal, vol. 94, pp. 777-786, Nov.-Dec. 1997.

J. Y. Zhu and J. S. Popovics, "Imaging concrete structures using air-coupled impact-echo," Journal of Engineering Mechanics-ASCE, vol. 133, pp. 628-640, Jun. 2007.

B. A. Mazzeo, A. N. Patil, R. C. Hurd, J. M. Klis, T. T. Truscott, and W. S. Guthrie, "Air-Coupled Impact-Echo Delamination Detection in Concrete Using Spheres of Ice for Excitation," Journal of Nondestructive Evaluation, pp. 1-10, Jul. 12, 2013 2013.

B. A. Mazzeo, A. N. Patil, and W. S. Guthrie, "Acoustic impact-echo investigation of concrete delaminations using liquid droplet excitation," NDT&E International, vol. 51, pp. 41-44, 2012.

B. A. Mazzeo, T. T. Truscott, and W. S. Guthrie, "Signal processing of acoustic impact response for reinforced concrete testing using paintballs and airsoft pellets for excitation," Audio and Acoustic Signal Processing Technical committee Newsletter, vol. 1, 2014.

International Search Report and Written Opinion received for PCT Patent Application No. PCT/US2015/039835 mailed Oct. 29, 2015, 17 pages.

Zagoudis, Jeff, "(Bridge) inspector", Roads & Bridges, pp. 34-38, May 2014.

La, Hung M. et al., "Mechatronic Systems Design for an Autonomous Robotic System for High-Efficiency Bridge Deck Inspection and Evaluation", IEEE/ASME Transactions on Mechatronics, vol. 18, No. 6, pp. 1655-1664, Dec. 2013.

"The future of bridge health management", Transportation Today, Rutgers Center for Advanced Infrastructure and Transportation, Newsletter Issue 11, 11 pages, Jan. 2013.

La, Hung Mahn et al., "Visual and Acoustic Data Analysis for the Bridge Deck Inspection Robotic System", The 31st International Symposium on Automation and Robotics in Constructions and Mining (ISARC) 2014, 8 pages.

"Vehicle-Mounted Bridge Deck Scanner", Final Report for Highway IDEA Project 132, 94 pages, Aug. 2010.

"Investigation of Full-Lane Acoustic Scanning Method for Bridge Deck Nondestructive Evaluation", Final Report for Highway IDEA Project 134, 29 pages, Nov. 2010.

\* cited by examiner

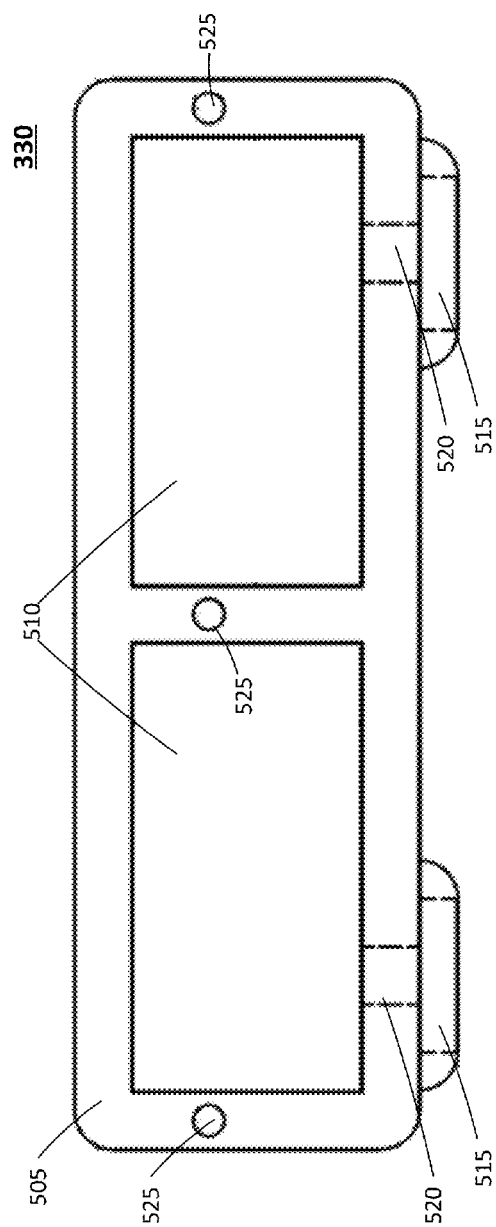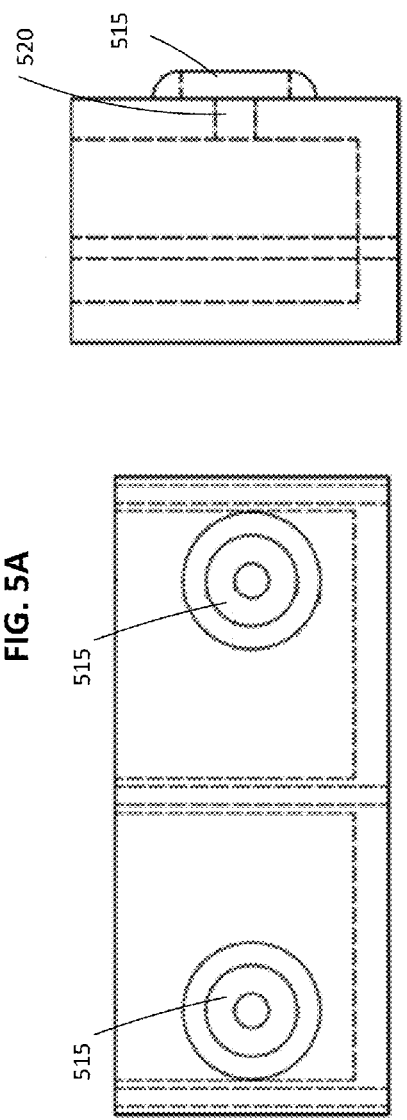
FIG. 5A
FIG. 5B
FIG. 5C

MULTICHANNEL IMPACT RESPONSE FOR MATERIAL CHARACTERIZATION

This application claims the benefit of U.S. Provisional Patent Application 62/022,489 filed on Jul. 9, 2014, entitled "REPEATED IMPACTS BY MALLET IMPACTOR FOR ACOUSTIC DEFECT EXCITATION IN MATERIALS WITH SIGNAL PROCESSING FOR AUTOMATED DEFECT MAPPING", U.S. Provisional Patent Application 62/115,144 filed on Feb. 11, 2015, entitled "MULTICHANNEL IMPACT RESPONSE FOR SUBSURFACE MATERIAL CHARACTERIZATION" and U.S. Provisional Patent Application 62/162,413 filed on May 15, 2015, entitled "AUTOMATIC MARKING OF A SURFACE TRIGGERED BY NON-DESTRUCTIVE MEASUREMENTS OF THE SURFACE PROPERTIES", the entire contents each of which are incorporated in their entirety herein by reference. This application is related to a co-pending Patent Cooperation Treaty (PCT) application entitled "MULTICHANNEL IMPACT RESPONSE FOR MATERIAL CHARACTERIZATION", PCT/US15/39835, the entire contents of which are incorporated herein by reference.

FEDERALLY SPONSORED RESEARCH

This invention was made with government support under contract W91156-12-P-0185 awarded by ARMY/AFRL. The government has certain rights in the invention.

FIELD

Embodiments relate to non-destructive characterization of materials (e.g., concrete). Embodiments relate to characterizing (e.g., finding defects, identifying discontinuities, measuring stiffness) the surface and/or subsurface of the material.

BACKGROUND

Concrete can be used in construction (e.g., roadways, bridges, and buildings) and has other uses in society. Over time, concrete can undergo reductions in strength and/or stiffness and can develop cracks and structural flaws, including but not limited to delaminations. This deterioration can be caused by age, weather, stress, etc. of the concrete. Methods for rapid scanning and identification of some forms of deterioration, including delaminations, are limited, and existing technology may not identify flaws or non-uniformities in concrete in a timely manner.

SUMMARY

In a general aspect, a non-destructive test system is disclosed. The non-destructive test system includes a plurality of impact devices including a knob configured to generate at least one flexural mode in a material when a surface of the material is impacted by the knob, a controller configured to independently control each of the plurality of impact devices, the controller having a communications channel for each of the plurality of impact devices, and a microphone configured to detect an acoustic response generated upon impact of the knob on the surface of the material, the acoustic response being based on the at least one flexural modes generated in the material.

Another non-destructive test system includes a plurality of impact devices including a knob configured to generate at least one flexural mode in a material when a surface of the material is impacted by the knob, a controller configured to independently control each of the plurality of impact devices, the controller having a communications channel for each of the plurality of impact devices, and an encoder configured to generate a signal based on a bounce of the knob off the surface after impact on the surface.

In yet another general aspect, a method for non-destructive test system is disclosed. The method includes triggering a release of a first impact device of a plurality of impact devices by a controller, triggering a release of a second impact device of the plurality of impact devices by the controller, detecting at least one first acoustic wave associated with a first portion of a surface resulting from an impact by the first impact device, detecting at least one second acoustic wave associated with a second portion of a surface resulting from an impact by the second impact device, identifying a first characteristic in the first portion of the surface based on the at least one first acoustic wave, and identifying a second characteristic in the second portion of the surface based on the at least one second acoustic wave.

Implementations can include one or more of the following features. For example, the non-destructive test system can further include an encoder configured to generate a signal based on a bounce of the knob off the surface after impact on the surface. The plurality of impact devices can be attached to a trailer configured to traverse the surface, the plurality of impact devices can be communicatively coupled to each other using an Ethernet protocol, and the plurality of impact devices can be communicatively coupled to the controller using the Ethernet protocol, each of the plurality of impact devices having a different address. The controller can be further configured to determine a characteristic at a location associated with the impact of the knob. The non-destructive test system can further include a marking device configured to mark the surface at the location of the characteristic. The non-destructive test system can further include a marking device configured to mark the surface with a mark at an interval, to photograph the mark, to determine a location of the mark and to associate the photograph with the location. The controller can be further configured to determine a characteristic at a location associated with the impact of the knob. The controller can be further configured to generate a map indicating the location of the characteristic.

The controller can be further configured to determine a characteristic at a location associated with the impact of the knob. Determining the characteristic can include at least one of time domain filtering, frequency domain filtering and signal separation of an acoustic wave detected by the microphone. Time domain filtering can include band pass filtering using a window that passes acoustic waves representing the impact. Frequency domain filtering can include converting the acoustic wave into the frequency domain, determining a center frequency of a contour, and identifying a characteristic based on the center frequency of the contour and a threshold value. Signal separation can include separating impact acoustic waves from noise using an eigenvalue analysis of a matrix-pencil.

The microphone can be a first microphone, the system can further include a second microphone configured to detect the acoustic response generated upon impact of the knob on the surface of the material, the acoustic response being based on the at least one flexural modes generated in the material. The controller can be further configured to determine a characteristic at a location associated with the impact of the knob based on a time difference between detecting the acoustic response at the first microphone and detecting the acoustic response at the second microphone and a distance between the first microphone and the second microphone. The plurality of impact devices can be attached to a trailer configured to traverse the surface. The trailer can be configured to be collapsed for transport between test sites.

The method can further include generating a first bounce signal based on a bounce off the first portion of a surface after impact associated with the first impact device on the first portion of a surface and generating a second bounce signal based on a bounce off the second portion of a surface after impact associated with the second impact device on the second portion of a surface. Identifying the first characteristic in the first portion of the surface is based on the first bounce signal, and identifying the second characteristic in the second portion of the surface is based on second bounce signal. The method can further include marking the first portion of the surface at a location of the first characteristic and marking the second portion of the surface at a location of the second characteristic. The method can further include marking the surface with a mark at an interval, photographing the mark, determining a location of the mark, and associating the photograph with the location. Detecting the at least one first acoustic wave reflected from the first portion of the surface resulting from the impact by the first impact device can include using a first microphone to detect a first of the at least one first acoustic wave and using a second microphone to detect a second of the at least one first acoustic wave.

Identifying the first characteristic in the first portion of the surface is based on a time difference between detecting the first of the at least one first acoustic wave at the first microphone and detecting the second of the at least one first acoustic wave at the second microphone and a distance between the first microphone and the second microphone. Triggering a release of a first impact device of a plurality of impact devices by a controller and triggering a release of a second impact device of the plurality of impact devices by the controller are based on determining a timing at which each of the plurality of impact devices are to initiate an impact test.

BRIEF DESCRIPTION OF THE DRAWINGS

Example embodiments will become more fully understood from the detailed description given herein below and the accompanying drawings, wherein like elements are represented by like reference numerals, which are given by way of illustration only and thus are not limiting of the example embodiments and wherein:

FIGS. 5A, 5B, and 5C illustrate views of a microphone housing according to at least one example embodiment.

Figure 1:
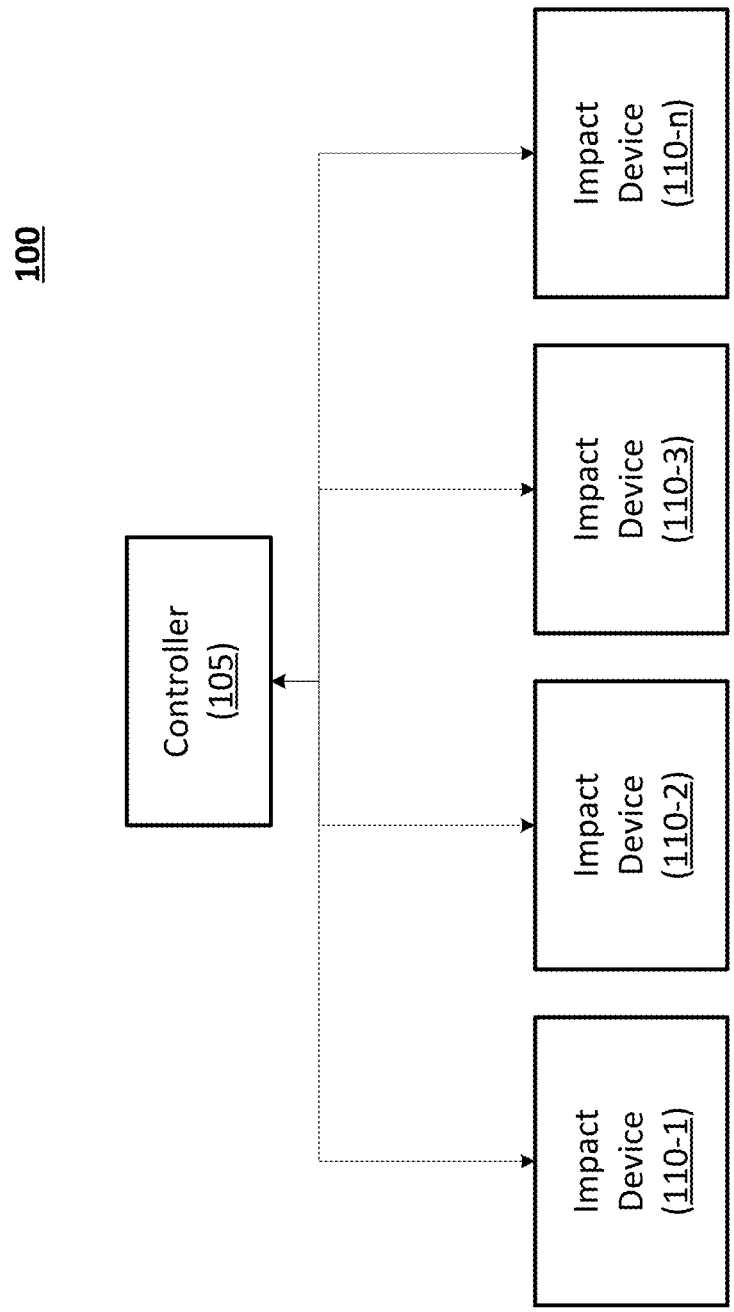
FIG. 1 illustrates a block diagram of a system according to at least one example embodiment.

It should be noted that these figures are intended to illustrate the general characteristics of methods, structures, and/or materials utilized in certain example embodiments and to supplement the written description provided below. These drawings are not, however, to scale and may not precisely reflect the precise structural or performance characteristics of any given embodiment, and should not be interpreted as defining or limiting the range of values or properties encompassed by example embodiments. For example, the relative thicknesses and positioning of structural elements may be reduced or exaggerated for clarity. The use of similar or identical reference numbers in the various drawings is intended to indicate the presence of a similar or identical element or feature.

DETAILED DESCRIPTION OF THE EMBODIMENTS

While example embodiments may include various modifications and alternative forms, embodiments thereof are shown by way of example in the drawings and will herein be described in detail. It should be understood, however, that there is no intent to limit example embodiments to the particular forms disclosed, but, on the contrary, example embodiments are to cover all modifications, equivalents, and alternatives falling within the scope of the claims. Like numbers refer to like elements throughout the description of the figures.

In order to scan a bridge, a trailer (approximately the width of a standard car lane or 12 feet wide) can be equipped with automated impact devices spaced evenly across the trailer (e.g., every 2 feet for a total of 7 mallets). These impact devices can be configured to strike the road, and, as the trailer is moved across one lane at a time at a relatively constant speed (e.g., about 2 feet per second), data can be recorded. A bridge location can be associated with each impact using a distance encoder mounted to the trailer (e.g., on an axle of the trailer). By analyzing an acoustic response, impact characteristics, and/or the frequencies generated with each impact, whether a specific impact occurred at a delaminated or intact location can be determined. Once location and acoustic response are meshed together, a complete bridge map revealing locations of all the defects, discontinuities, changes in stiffness, etc. can be generated. This method can be faster, cheaper, and more reliable than methods currently in use.

In an example implementation, there can be seven impact devices, one distance measuring unit, and a computer on the trailer. The distance encoder can measure distance traveled and time. Computer commands can be generated, causing the impact devices to be released and generate the impact based on this distance and time. Each impact device hits the road individually (e.g., one at a time) so as to avoid signal interference with the other units. The impact device can be configured to release a mallet, sample the impact using a microphone(s) and/or angle encoder, send the data to the computer, and reset the impact device for the next impact. The seven impact devices can operate in a coordinated manner such that each mallet unit is operated in sequence to perform a test along the surface.

The computer can be configured to communicate with the impact devices using a wired or wireless protocol. For example, the computer can be configured to communicate with the mallet unit using an Ethernet protocol.

FIG. 1 illustrates a block diagram of a system according to at least one example embodiment. As shown in FIG. 1, the system 100 includes a controller 105 and impact devices 110-1, 110-2, 110-3, 110-n. Although four impact devices are shown, example embodiments are not limited thereto. The controller 105 may be a multi-channel controller. In other words, controller 105 may include a separate control channel for each impact device 110-1, 110-2, 110-3, 110-n. As such, the controller 105 can individually control each impact device 110-1, 110-2, 110-3, 110-n. The controller 105, the impact device 110-1, 110-2, 110-3, 110-n, and other devices (e.g., the aforementioned computer) can be communicatively coupled using a 16-port Ethernet switch.

Impact devices 110-1, 110-2, 110-3, 110-n may be configured to capture (acquire and/or detect) test data characterizing a material (e.g., pavement or concrete) based on an impact on the material. The test data may be used to determine a quality characteristic of the material. The quality characteristic of the material may be, for example, surface and/or subsurface concrete defects, discontinuities, and/or changes in stiffness (e.g., based on Young's modulus) associated with the material. In other words the impact devices 110-1, 110-2, 110-3, 110-n may be configured to capture test data identifying flaws in a material (e.g., pavement or concrete). The system 100, including the controller 105 and the impact devices 110-1, 110-2, 110-3, 110-n, may be configured to capture test data in a larger system implementing an acoustic impact-echo method.

The acoustic impact-echo method can be a functional technique used to find and identify surface and/or subsurface concrete (or other material) characteristics or quality characteristics. These can include defects, discontinuities, and/or changes in stiffness. Hereinafter references to characteristics or quality characteristics, defects, discontinuities, stiffness and/or changes in stiffness can be used interchangeably. This technique can include striking the concrete surface with an impactor (e.g., as an element of an impact device 110-1, 110-2, 110-3, 110-n), sometimes called a mallet, listening to an echo generated as a result of the impact, and evaluating the structural state of the concrete (pavement and/or other structural materials) based on a frequency component(s) of the echo. The acoustic impact-echo method is similar to knocking on a wall and listening to the echo in order to locate the studs within the wall. For example, as the knocking is on (or close to) a position including a stud, the sound (or frequency response) of the echo changes as compared to the cavity between the studs.

As the flexural modes of concrete are excited by an impact, the concrete resonates at different audible frequencies based on the integrity (consistency or continuity) of the concrete (surface and subsurface) at the location of excitation (by the impact). These flexural frequencies differ between intact and broken areas within the concrete, or between areas having different quality characteristics. The information stored within the acoustic energy resulting from an impact at a particular point can indicate the concrete's structural integrity. Current methods for excitation involve chaining and other processes that are time-consuming and somewhat inaccurate. For example, some of these methods can require drilling into a bridge deck.

The flexural modes of concrete are excited by an impact using non-destructive testing techniques and destructive testing. For example, a non-destructive testing technique can include chaining, which involves dragging a chain across the structure and listening (e.g., by a human operator traversing the test surface with the chain) to the resulting sound. As the chain is dragged across an intact location, the chain produces a high-frequency ringing sound. Dragging the chain across a delaminated spot produces a relatively low-frequency hollow sound, which can be audible. Chain dragging over a delaminated spot can produce the higher-frequency ringing sound and the lower-frequency hollow sound. In other words, the total acoustic spectra can change at a delaminated spot to include the lower-frequency hollow sound. For example, higher-frequency components can be induced because of reflections, known as Lamb waves, between the top of the concrete and the crack boundary. Upon finding these delaminated spots, an operator can record the location of delamination and continues across the bridge. The chaining method can be error-prone because, for example, the worker may be unable to distinguish between sounds produced from intact and delaminated spots due to ambient noise, the worker may be distracted or fatigued, the worker could accidentally miss a spot or mark a delamination in an incorrect location, the size of a delamination could be inaccurately recorded, and/or many other potential issues. Accordingly, a more reliable, more accurate, and faster method of non-destructively finding delaminations and indicating (e.g., generating a map of) structural flaws is desirable.

According to example embodiments, a non-destructive testing technique can include using signal processing techniques to indicate (e.g., mark the surface and/or generate a map of) quality characteristics of a surface and/or subsurface of a material. Indications can be generated based on differing impact response frequencies measured in response to an impact on the surface (e.g., concrete). In other words, frequencies associated with an echo after an impact can be measured and used to determine if there are flaws in the material (surface and/or subsurface) of the structure (e.g., road, bridge, wall, dam, parking lot, parking garage, and/or the like). By striking the surface (e.g., concrete) with an impactor (e.g., a mallet), recording the acoustic or frequency response, and then moving to the next location, the structure (e.g., road, bridge, wall, dam, parking lot, parking garage, and/or the like) can be scanned quickly, and a reliable indication of flaws (e.g., a surface mark and/or a map) can be generated.

Figure 2:
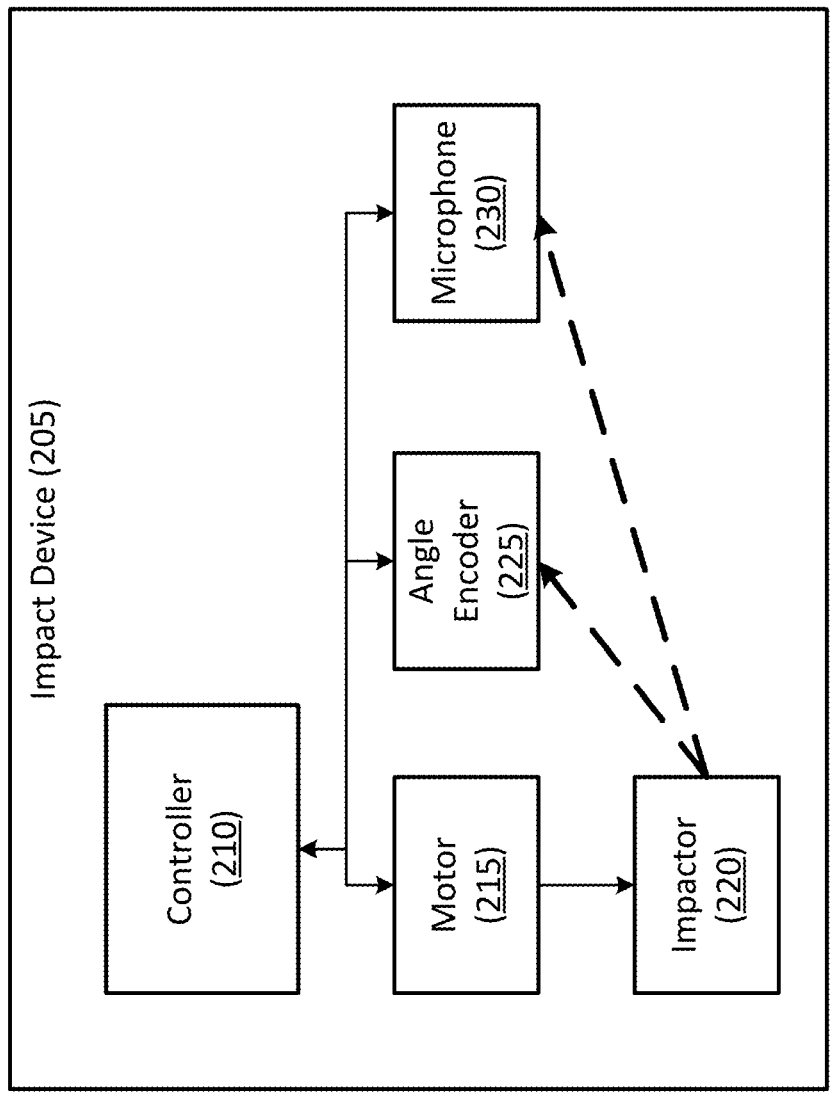
FIG. 2 illustrates a block diagram of electrical or electronic elements of an impact device according to at least one example embodiment.

FIG. 2 illustrates a block diagram of electrical or electronic elements of an impact device according to at least one example embodiment. As shown in FIG. 2, the impact device 205 (e.g., one of impact devices 110-1, 110-2, 110-3, 110-n) can include a controller 210, a motor 215, an impactor 220, an angle encoder 225, and a microphone 230. The controller 210 can be configured to trigger an impact by the impactor 220 by controlling (e.g., sending a signal or applying a voltage to) the motor 215 to turn and release the impactor 220 (or cause the impactor 220 to be released). The controller 210 can be further configured to receive a signal from the microphone 230. The signal from the microphone 230 can include frequency information (e.g., acoustic and/or frequency responses) associated with an impact of the impactor 220 on a surface (e.g., concrete, pavement, and/or the like). The controller 210 can be further configured to receive a signal from the angle encoder 225. The signal from the angle encoder 225 can include information indicating a height or distance the impactor 220 bounces with respect to the surface after impact. For example, the rebound can be measured by counting the angle of rotation at the fulcrum of the shaft 315 and/or knob 320. The information recorded by the angle encoder 225 about recoil can be used in conjunction with the microphone data to help determine where delaminations are located. This can be done because the shaft 315 may have a shallower rebound after striking delaminated concrete than the rebound associated with intact concrete. This can occur because the stiffness of the concrete is reduced at the location of a delamination, which then causes a longer contact time and a greater transfer of kinetic energy to the concrete so that the rebound is less. In other words, delaminated concrete absorbs more of the impact, and thus the knob 320 has a lower rebound. The rebound measurements can be another technique for identifying subsurface flaws apart from acoustic response and wave speed (discussed with regard to FIG. 16 below).

Processing the recorded audio can involve several steps. First, a threshold detector followed by a time separator can be used to determine when impacts occur within the recording. Alternatively, or in addition to, impacts and impact data can be stored with an associated time stamp. Then, the energy in a band of signals during the first milliseconds after the impact can be computed by summing coefficients in a Fast Fourier Transform (FFT) of the signals, and the energy can also be plotted. These energies of the different frequency components can then be used to classify a severity of a delamination, or a degree of deterioration, discontinuity, etc. The information within the acoustic response can be extracted and used for multiple analyses.

The microphone 230 can also include a recorder. For example, the microphone 230 can be a piezoelectric array microphone together with an acoustic sampling unit. The detector may also be a fiber optic microphone, a laser microphone, a silicon-based microphone, a moving coil microphone, and the like. The recorder (or acoustic sampling unit) may be an element of the controller 105. The microphone 230 may be close (or substantially close) to the surface. For example, the microphone 230 may be within 8, 12, 20, 25 cm of the surface (e.g., of the impact point) and directed towards the impact location.

Figure 3:
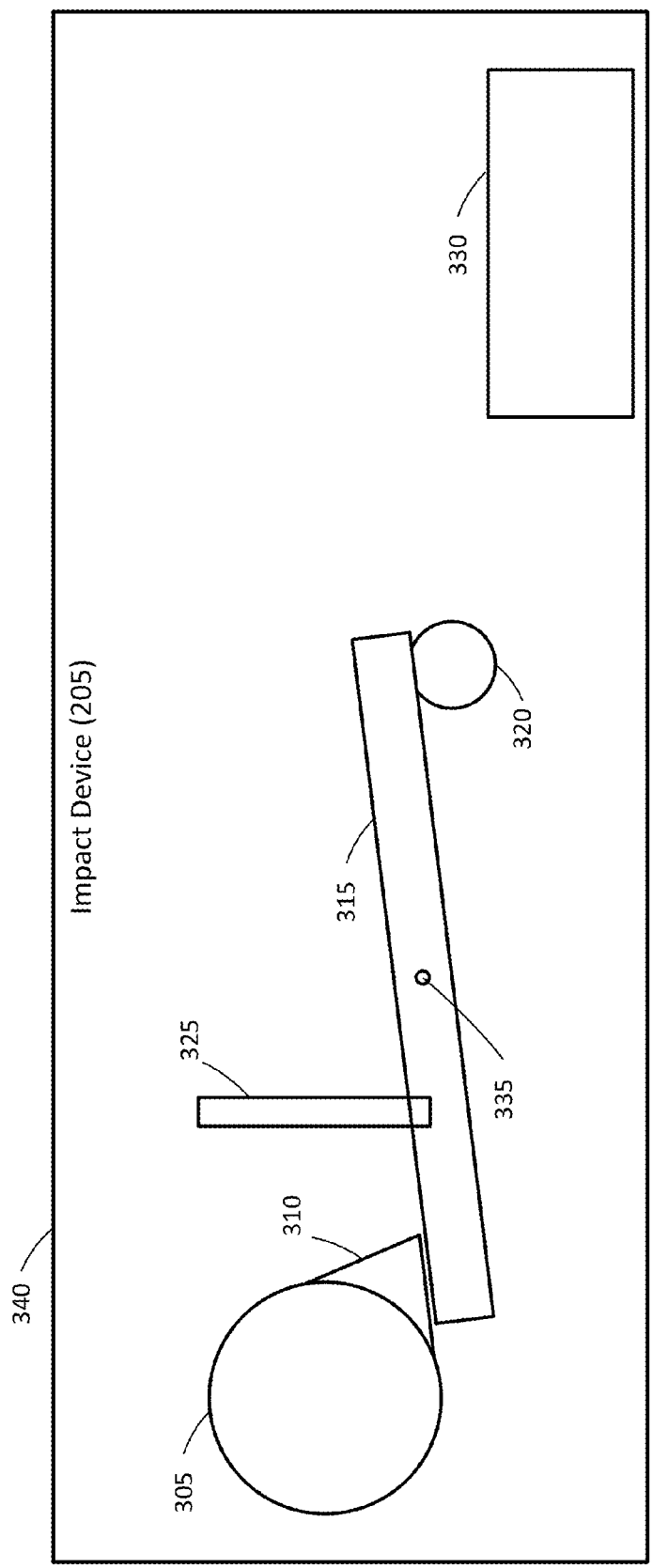
FIG. 3 illustrates a block diagram of mechanical elements of an impact device according to at least one example embodiment.

FIG. 3 illustrates a block diagram of mechanical elements of an impact device according to at least one example embodiment. As shown in FIG. 3, the impact device 205 (e.g., one of impact devices 110-1, 110-2, 110-3, 110-n) can include a cam 305, a shaft 315, a knob 320, a tension unit 325, and a microphone housing 330. The shaft 315 may pivot or rotate around element 335. The shaft 315 can be constructed of polypropylene. Polypropylene can increase the contact time of the knob 320 and the surface, which then causes more significant energy transfer and/or greater deflection of the surface. In other words, polypropylene is a strong, yet flexible plastic that bends to allow more full contact with the road, yet rigid enough to allow accuracy in angle measurements. Polypropylene can help control a contact time (of the knob 320) with the road because these flexural modes are best excited when struck with a hard but lasting impact. Element 335 may be a pin. The cam 305 may include a contact portion 310 configured to hold (or help hold) and release (or help release) the shaft 315. The tension unit 325 may be, for example, a spring or a piston. The tension unit 325 can be configured to pull or force the shaft 315 to rotate such that the side of the shaft 315 including the knob 320 is moved toward and forced to contact a surface (e.g., road, bridge, wall, dam, parking lot, parking garage, and/or the like). Plate 340 may be a mounting plate on which the components (e.g., electronic and mechanical) can be mounted.

The knob 320 can be designed and constructed so as to produce a desirable response upon impact. While many different materials can produce an echo when striking the surface, a material (and shape) of the knob 320 can be selected to excite the flexural modes of the material and cause the delaminations to resonate distinguishably. For example, symmetrical Lamb waves can move in a symmetrical fashion about the median plane of the surface. This is sometimes called the extensional mode because the wave is stretching and compressing the material in the wave motion direction. Wave motion in the symmetrical mode is most efficiently produced when the exciting force is parallel to the surface. The asymmetrical Lamb wave mode is often called the flexural mode because a large portion of the motion is in a direction normal to the surface, and a little motion occurs in the direction parallel to the surface. Materials that are more flexible, in general, have a longer residence time during impact and so have an improved response when used in terms of exciting the low-frequency flexural modes generally associated with delaminations. For example, knob 320 can be constructed of phenolic resin or brass. Knob 320 can be constructed of other materials that are solid and generate the desired flexural modes (e.g., it can be desirable for the knob 320 to be constructed of a material that is not as hard as steel). In conjunction with the shaft 315 being constructed of polypropylene, a significant impact for generating a preferred type of echo can be accomplished.

According to an example implementation, controller 210 causes the motor 215 to turn, causing the cam 305 to turn. The contact portion 310 then disengages from the shaft 315. The tension unit 325 is released, causing the shaft 315 to rotate. When the shaft 315 rotates, the knob 320 drops with a force and impacts the surface. When the knob 320 impacts the surface, an acoustic or frequency response is generated, which is then detected by the microphone 230. The acoustic or frequency response is converted to an electrical representation by the microphone 230, which is then communicated to the controller 210. Following impact, the knob 320 bounces or rebounds off of the surface. This bounce or rebound is converted by the angle encoder 225 to a height or distance from the surface electrical representation, which is then communicated to the controller 210.

Figure 4:
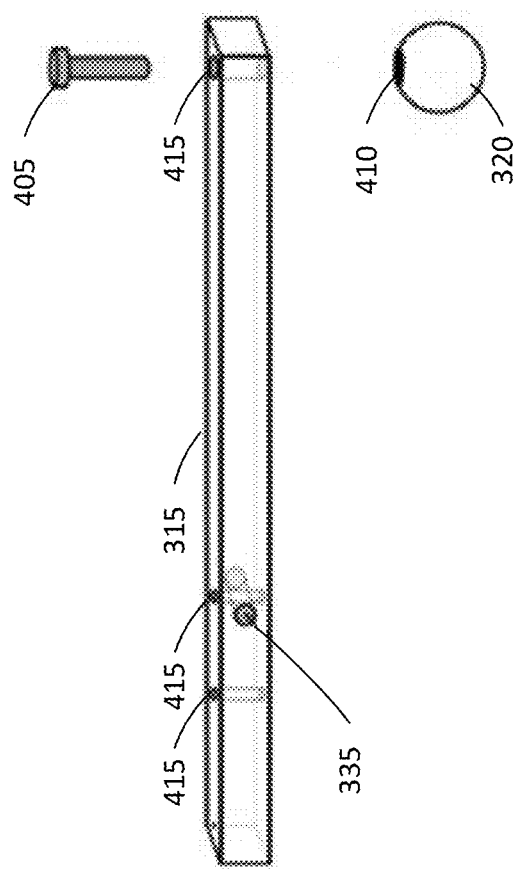
FIG. 4 illustrates detail regarding the shaft shown in FIG. 3 according to at least one example embodiment.

FIG. 4 illustrates additional detail regarding the shaft 315. As shown in FIG. 4, the shaft 315 includes a number of holes 415. The holes 415 may be threaded or smooth. The holes 415 may be configured to allow other elements to be attached to the shaft 315. For example, knob 320 can include an internal threaded portion 410. Using one of the holes 415, the knob can be attached to the shaft 315 with a bolt 405 threaded into a threaded portion 410. Further, the tension unit 325 may be attached to the shaft 315 using one of the holes 415. Still further, the shaft can be mounted to the plate 340 using, for example, element 335 (as a pin) and a cotter pin or set screw threaded into one of the holes 415. Although shown as a sphere, knob 320 can be formed in other shapes (e.g., oblong, a pyramid, a cylinder, and the like).

FIGS. 5A-5C illustrate various views of the microphone housing 330. The microphone housing 330 can be a box constructed using a 3D printing process. The housing box can be insulated with foam to provide external sound dampening. FIG. 5A illustrates a side view of the microphone housing 330. As shown in FIG. 5A, the microphone housing 330 includes an enclosure 505. The enclosure includes a number of voids 510 formed between portions of the enclosure 505. In an example implementation, each void 510 can include a microphone. Alternatively, each void 510 can include the microphone and microphone support equipment (e.g., an amplifier). FIG. 5B illustrates a bottom view of the microphone housing 330. As shown in FIG. 5B, the microphone housing 330 can include a funnel 315 configured to funnel sound (e.g., an acoustic or frequency response to an impact) to the microphone. Funnel 315 can also be configured to block ambient noise (e.g., sound waves not generated at the impact point below the microphone). FIG. 5C illustrates another side view of the microphone housing 330. As shown in FIGS. 5A and 5B, the microphone housing 330 includes a channel 520 through which the sound can be directed to the microphone (not shown). As shown in FIG. 5A, the microphone housing 330 can include holes 525 used to (or used to help) mount the microphone housing to the plate 340.

As is shown in FIGS. 5A and 5B, the microphone housing 330 can include more than one microphone. For example, the illustrated microphone housing 330 is configured to house at least two microphones. In an example implementation, the at least two microphones can have different and/or overlapping frequency responses, frequency ranges, and/or frequency sensitivities. For example, one of the at least two microphones could be configured for low-frequency responses and another of the at least two microphones could be configured for high-frequency responses. The at least two microphones could have overlapping frequency responses in order to cover mid-range frequencies. Selection of the at least two microphones could be based on the material of the surface to be tested and/or the type of surface to be tested. For example, testing a bridge constructed with an asphalt (or relatively soft) surface could potentially be performed using a different microphone configuration than that used when testing a roadway constructed with a concrete (or relatively hard) surface.

In addition, having two microphones can allow for calculation of the wave speed within the concrete. This can be done by placing the microphones approximately 12 cm apart (or closer or farther, as desired) to identify the time difference in echo reception between the two microphones. This arrival time can be associated with the microphone spacing and can help to determine how fast the wave is actually moving within the concrete. Intact concrete is stiffer (it has a higher Young's modulus) than deteriorated concrete (cracked concrete or concrete with higher porosity), resulting in faster wave speeds in intact concrete than in deteriorated concrete. Intact concrete has fewer defects, discontinuities, etc., and thus the wave will travel faster when compared to a wave travelling within deteriorated concrete. This wave speed can be used as another indicator of deterioration (e.g., delamination) rather than strictly using acoustic response.

In an example implementation, each void 510 can include a microphone. Any support equipment (e.g., an amplifier) can be housed separately and be communicatively coupled to the microphone. Alternatively, each void 510 can include a microphone and microphone support equipment (e.g., an amplifier). The support equipment can be associated with a microphone amplifier. The amplifier can be, for example, a two-stage op-amp. The amplifier may be configured to amplify a signal to a desired level while eliminating (or substantially eliminating) as much noise as possible. The example amplifier may have several gain settings in order to achieve a desired gain. For example, the gain settings can be used until achieving a gain of about ½. A gain of about ½ can avoid clipping of the analog-to-digital converters (ADCs) on the microcontroller after listening to a loud impact.

Figure 6A:
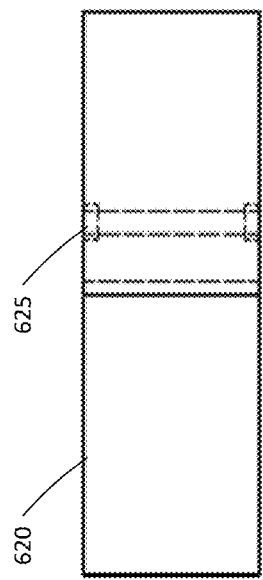
FIGS. 6A, 6B, 6C, and 6D illustrate block diagrams of elements of the impact device according to at least one example embodiment.
Figure 6B:
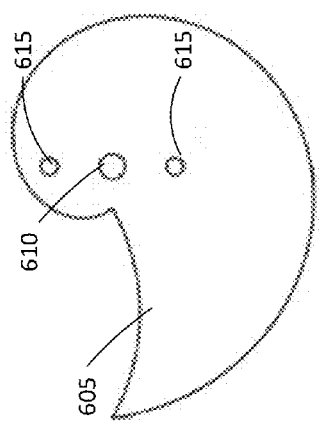
Figure 6D:
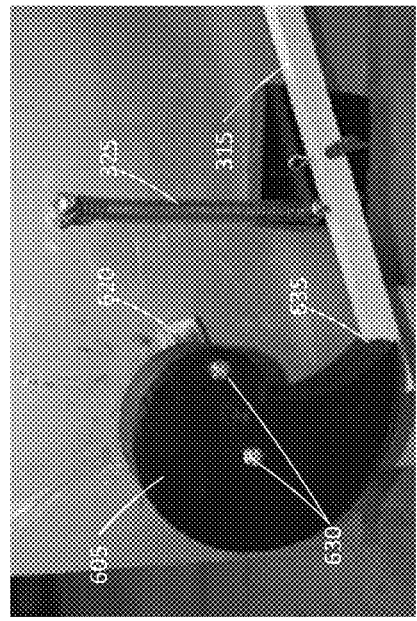
Figure 6C:
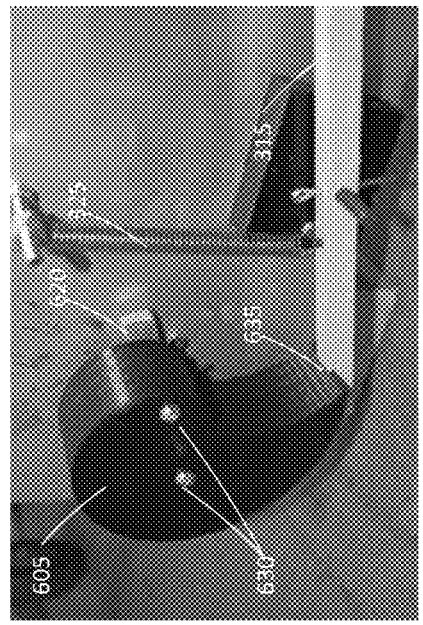

An example cam (e.g., cam 305) is illustrated in FIG. 6A. As shown in FIG. 6A, the cam 605 can be in the shape that resembles an asymmetrical coil, an asymmetrical spiral, and/or a snail shell. Accordingly, the cam 605 may also be referred to as a snail cam. However, the cam 305 illustrated in FIG. 3 is not so limited. The cam 605 can be attached to a shaft associated with the motor 215 by using a roll pin inserted through hole 610. The roll pin can go through both the cam 605 and a spacer 620 (illustrated in FIG. 6B) and helps hold them together with screws 630 (illustrated in FIGS. 6C and 6D). As shown in FIGS. 6C and 6D, a notch 635 in either the cam 605 or the shaft 315 can be configured to allow the cam 605 to rest before another impact and help hold the shaft 315 in the desired resting position. Using the motor 215, a small reverse pulse can be applied to the cam 605 to help ensure the cam 605 locks against the shaft 315 in a desired starting, or reset, position.

The snail shell shape of the cam of FIG. 6A can be designed to provide a gradual reset of the shaft 315 rather than a swift impact on the shaft 315 to drive the shaft 315 into a reset position. The gradual reset can eliminate (or reduce) instability resulting from oscillations and bouncing of the shaft 315 during reset. The snail shell shape may be configured as a uniformly increasing radius while rotating around the shell center. This cam can be 3D printed, using for example, the same material used for the microphone housing 330.

Figure 7A:
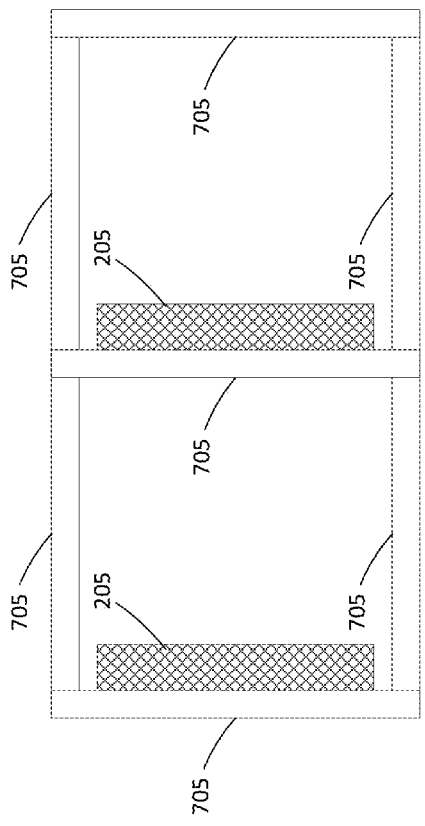
FIGS. 7A and 7B illustrate a trailer according to at least one example embodiment.
Figure 7B:
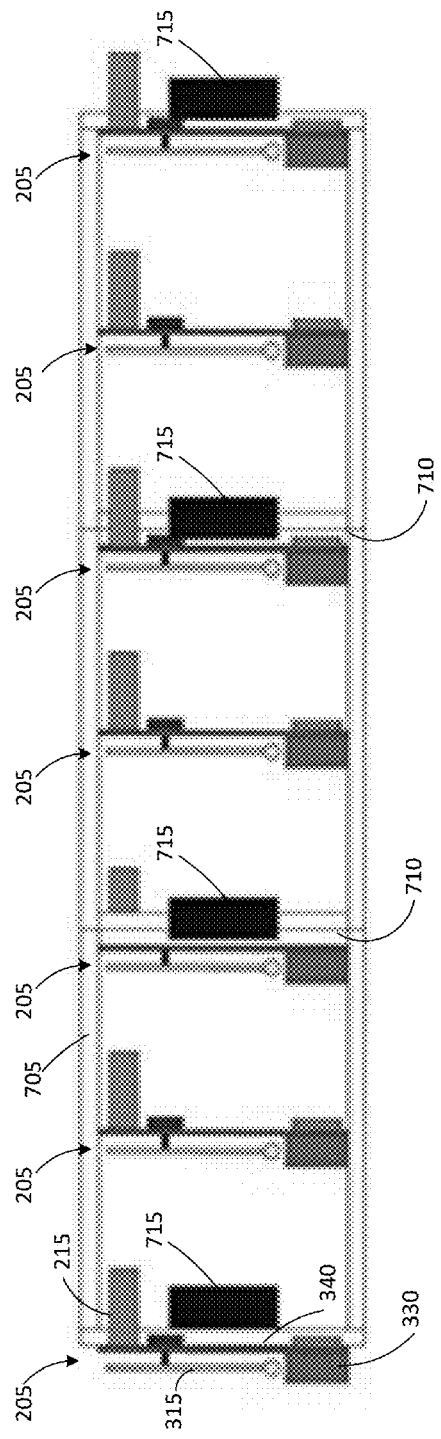

FIG. 7A is a block diagram of a trailer or a portion of a trailer or trailer frame. As is shown in FIG. 7A, the trailer can include a number of frame members 705 on which an impact device 205 can be attached. FIG. 7B is a schematic of the trailer with an array of impact devices 205 (e.g., seven impact devices 205). Each impact device 205 can be mounted to a cross beam that runs parallel to the trailer. The spacing of each mallet can make it possible to generate impacts, listen to the response, and evaluate structural integrity of, for example, an entire lane width all at one time.

FIG. 7B is a top-down view of a trailer. The impact devices 205 can be variably and movably spaced based on a span of the surface to be tested. For example, the impact devices 205 can be spaced at 2 foot intervals to span a single lane of traffic on a bridge or highway. Hinges 710 between the trailer and the different sections allow for constrained but substantial movement to accommodate varying terrain. Each impact device 205 can receive power from an inverter (12V battery or alternator). A GigE Ethernet switch can enable communications between the impact devices 205. A distance encoder mechanism can be attached to one or more of the wheels 715 shown on the trailer. The distance encoder is attached to a pulley, which is attached by a belt to a pulley on a main axle. The frame can be light enough that it can be folded and managed by a single operator using, for example, a winch. For example, hinge 715 can be configured to allow the trailer to be folded so that the trailer can be placed in, for example, a truck bed for transport to and from test sites. A test site can be at a same location (e.g., on a same bridge) and/or a different location (e.g., on a different bridge).

In addition, the trailer can be configured to measure less than its full width. For example, the trailer can be configured to test a relatively narrow shoulder of a road, highway, or bridge. Accordingly, portions of the trailer can be folded and corresponding impact devices not used. According to an example embodiment, the trailer can be configured to have two (or more) hinged portions. As such, one can be lifted and removed from use in order to accommodate the width of the section of the roadway being tested. In an example arrangement, there is a first portion including one impact device on one side of the trailer and a second portion including two impact devices on the other side of the trailer in order to accommodate a variety of different scanning widths.

Using hitches or couplers, the trailer can attach to, for example, a 4'×4' trailer (e.g., including test control equipment; see below regarding FIGS. 11A and 11B). The trailer can hook to the hitch of a truck which can be the main driving unit. The hinges 715 between the two sections can be configured to allow the custom frame to be pulled up with a winch and suspended a desired height above the test surface when moving over uneven terrain, turning around, or making other movements that require that equipment to be elevated from the test surface. The frame illustrated in FIG. 7B can be broken up into 3 hinging sections. The main center piece can be attached to the trailer with the other two custom sections serving as folding wings attached to the main center piece.

Figure 8:
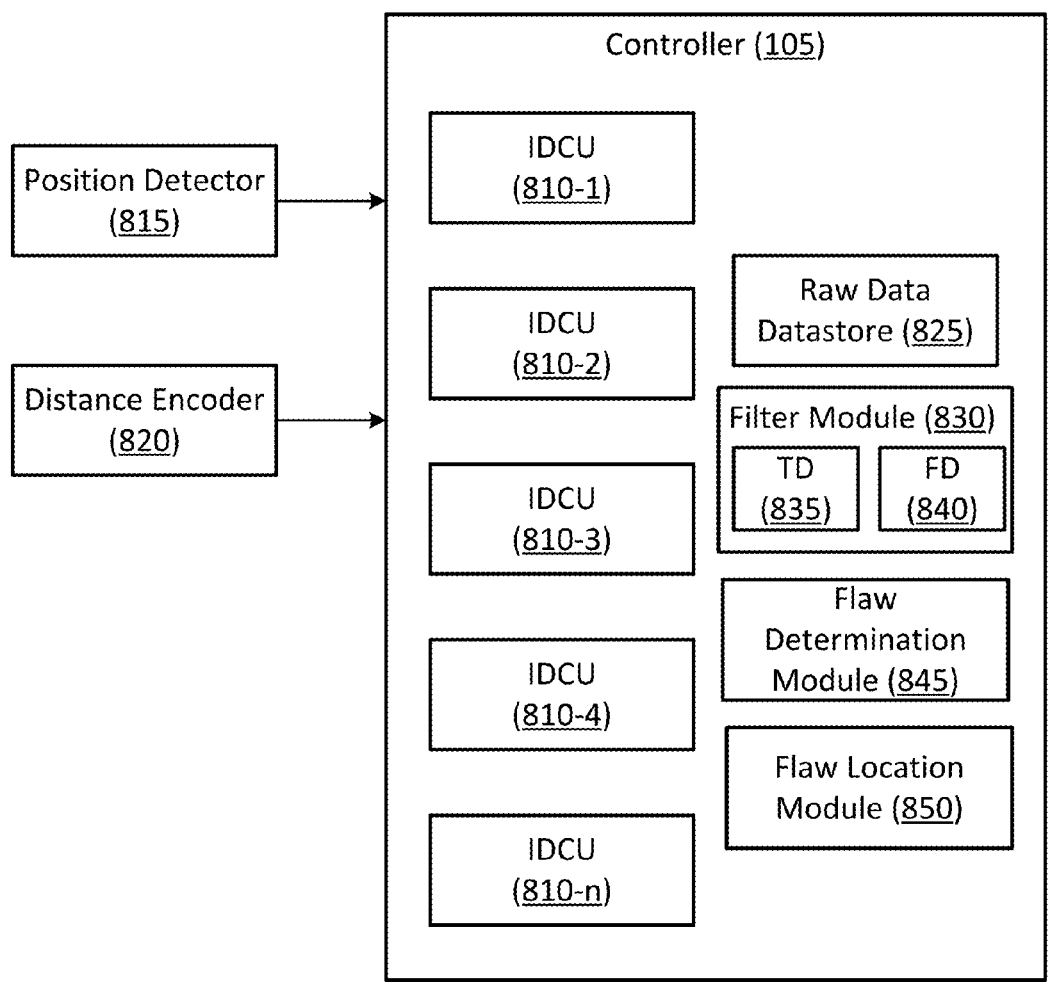
FIGS. 8, 9A, and 9B illustrate block diagrams of controllers according to at least one example embodiment.

FIG. 8 is a block diagram of the controller 105 illustrated in FIG. 1. As shown in FIG. 8, controller 105 can receive inputs from a position detector 815 and/or a distance encoder 820. The controller 105 can include a plurality of impact device control units (IDCU). The IDCUs are illustrated as IDCU 810-1, 810-2, 810-3, 810-4, 810-n. Although five IDCUs are shown, example embodiments are not limited thereto. For example, trailer illustrated in FIG. 7B could have an associated controller 105 including seven IDCUs. The controller 105 can further include a raw data datastore 825, a filter module 830, a flaw determination module 845, and a flaw location module 850. The filter module can include a time domain module 835 and a frequency domain module 840.

The position detector 815 can be configured to determine, calculate, and/or detect a position of the trailer and/or the impact device 205. The position detector 815 can determine a relative position (e.g., a start point of a test) and/or an absolute position based on, for example, a global position system GPS. The distance encoder 820 can be configured to determine a distance traveled by, for example, the trailer. The position detector 815 and/or the distance encoder 820 can be attached to the trailer in any way that helps the position detector 815 and/or the distance encoder 820 to perform its function. For example, the distance encoder 820 can be configured to determine the distance travelled based on a rotation of one or more of wheels 715. Therefore, the distance encoder can be coupled to one or more of wheels 715. For example, the distance encoder 820 can be configured to determine the distance travelled based on a rotation of a wheel attached to the distance encoder 820. The distance encoder 820 can be attached to the back of the frame of the trailer. The distance encoder 820 can be configured to roll along with the frame. The distance encoder 820 can be configured to send commands related to distance travelled.

Each IDCU 810-1, 810-2, 810-3, 810-4, 810-n can be configured to individually and/or independently control and receive data from an impact device 205. For example, each IDCU 810-1, 810-2, 810-3, 810-4, 810-n can control the timing and/or distance at which an impact device 205 generates test data based on an impact on a surface. Accordingly, a system including a plurality of impact devices 205 can acquire data across a large surface and/or rapidly scan a surface as the trailer including the impact devices moves across the surface. Each IDCU 810-1, 810-2, 810-3, 810-4, 810-n can be configured to communicate instructions to an impact device 205, receive data from an impact device 205, and generate test results based on the received data.

The data may be measurements associated with the knob 320 impacting the surface. The measurements may be acoustic waves and/or distance values. The measurements may indicate a defect (e.g., a delamination defect) in the concrete. The measurements may be stored in the raw data datastore 825. The measurements may be stored in the raw data datastore 825 together with information about the measurement (e.g., location and/or time). The measurements may be stored in correspondence with the associated impact times for an object. The position detector 815 may be configured to indicate a location of the impact. The indication of the location may be stored in correspondence with a measurement in the raw data datastore 825. In other words, the measurement for an acoustic wave associated with an impact may be stored, in the raw data datastore 825, with a corresponding location of the impact. The location of the impact can be determined based on timestamps in a post-process operation. For example, the angle encodings, the position (e.g., GPS), and photography can be used to determine a location as a function of time. Accordingly, the measurement for an acoustic wave associated with an impact may be stored, in the raw data datastore 825, with a corresponding timestamp (indicating the location) of the impact.

The flaw determination module 845 may be configured to determine whether a defect (e.g., a delamination defect) exists (or likely exists) in the concrete. The flaw determination module 845 may determine whether a defect exists based on the measurements (e.g., acoustic wave measurements). Accordingly, the flaw determination module 845 may be configured to read the measurements stored in the raw data datastore 616. Then the flaw determination module 845 may determine associations between acoustic wave measurements, object impact times, and impact locations (e.g., GPS positions).

The filter module 830 may be configured to filter (or remove) undesirable acoustic wave measurements. For each acoustic wave associated with an impact, acoustic waves representing noise or ambient noise (e.g., environmental sounds associated with nearby vehicles) or other undesirable sounds (e.g., spring or mechanical movements associated with a trailer or impact device) may be filtered from the acoustic wave measurements. For example, a time domain band reject filter having a window (e.g., a Hamming window) that excludes acoustic waves generated by a release of the shaft 315 and the corresponding compression of the tension unit 325 can be used. For example, a time domain band pass filter having a window that passes acoustic waves representing an impact of an object on concrete may be used. Accordingly, the filter module 830 includes a time domain module 835. In another example embodiment, the filter module 830 may be configured to detect an acoustic wave signature. For example, a first filter based on an expected wave for no defect may be developed and applied. For example, a second filter based on an expected wave for defect may be developed and applied. The output from applying the first or second filter may indicate whether or not a defect exists in the concrete.

Further, the acoustic waves representing an impact of the knob 320 on concrete may be filtered in the frequency domain to filter or remove acoustic waves representing ambient noise. For example, the acoustic waves (e.g., time domain filtered acoustic waves) representing an impact of an object on concrete may be converted (e.g., using a Fourier transform) to the frequency domain as, for example, contours having a center frequency based on the wavelength of the acoustic wave in the time domain. The frequency domain contours may be filtered to remove acoustic waves representing ambient noise. The frequency domain filter may remove contours having a center frequency below a set value. Accordingly, the filter module 830 includes a frequency domain module 840. Although the above description describes the time domain filtering occurring before the frequency domain filtering, in example embodiments the frequency domain filtering may be performed before the time domain filtering.

Further, a first order matrix pencil blind source separation (BSS) method using a smoothed spatial fourth-order cumulant matrix definition can be used where a noise environment is unpredictable (e.g., difficult to place computational restrictions on the noise). The fourth-order cumulants can be insensitive to either spatial or temporal correlation in Gaussian sensor noise since the higher-order cumulants of Gaussian random processes are zero. Therefore, BSS allows degrees of freedom to estimate a Gaussian noise subspace, making BSS capable of using all the degrees of freedom for separating as many sources as there are sensors (e.g., microphones) in an array. In order to estimate the adaptive complex sensor weights for separating the multiple sources, a spatial fourth-order cummulant matrix pair can be formed for two different sets of time lags between the observations from the different sensors. Accordingly, signal separation may be used to remove acoustic waves representing ambient noise. Signal separation may include separating impact acoustic waves from noise using an eigenvalue analysis of a matrix-pencil. Further, signal separation, time domain, and/or frequency domain filtering may be performed with or without the other type of filtering and/or signal separation.

The flaw determination module 845 may be configured to determine whether a defect (e.g., a delamination defect) exists (or likely exists) in the surface or subsurface based on at least one of the frequency domain, time domain filtered acoustic wave measurement(s) and the distance measurements. For example, frequency domain contour center frequencies may indicate the difference between a surface with a defect and a surface without a defect. Therefore, in one example embodiment, frequency domain contour center frequencies with values above a first threshold value may be associated with a surface with a defect, and frequency domain contour center frequencies with values below the first threshold value may be associated with a surface without a defect.

In another example embodiment, frequency domain contour center frequencies with values below a second threshold value may be determined as a surface with a defect, and frequency domain contour center frequencies with values above the second threshold value may be determined as a surface without a defect. In yet another example embodiment, frequency domain contour center frequencies with values between a third threshold value and a fourth threshold value may be associated with a surface with a defect, and frequency domain contour center frequencies with values not between the third threshold value and the fourth threshold value may be associated with a surface without a defect. In still another example embodiment, an angle value determined by the angle encoder (e.g., as a rebound distance) with a value below a threshold value may be associated with a surface with a defect, and an angle value determined by the angle encoder with a value above the threshold value may be associated with a surface without a defect. In other words, if the knob 320 rebounds above a threshold angle, there may be no defect.

The raw data datastore 825 can be configured to store data from each IDCU 810-1, 810-2, 810-3, 810-4, 810-n. The data can indicate the corresponding IDCU, can indicate the corresponding impact device 205, and can include the location of impact associated with the data. Accordingly, the flaw determination module 845 can be configured to determine if there are flaws at any location associated with data stored in the raw data datastore 825. The flaw location module 850 can be configured to store flaws in relationship to a location, generate a map of flaws, generate a signal based on a flaw, and/or the like. For example, the flaw location module 850 can be configured to generate a signal causing a marking of a surface based on a flaw. This marking can be in real time or be made in a subsequent pass (e.g., after the test) over the location. The flaw location module 850 can be configured to generate a map showing locations of flaws. The flaw location module 850 can be configured to generate a graph indicating flawed and non-flawed locations.

In an example implementation, each of the IDCU 810-1, 810-2, 810-3, 810-4, 810-n and each of the impact devices 110-1, 110-2, 110-3, 110-n can be the same except for using a unique IP address. When the impact device 110-1, 110-2, 110-3, 110-n is powered on, the IDCU 810-1, 810-2, 810-3, 810-4, 810-n turns on a light-emitting diode (LED) (e.g., a red LED) indicating the initialization phase of the IDCU 810-1, 810-2, 810-3, 810-4, 810-n. In this phase, the impact device 110-1, 110-2, 110-3, 110-n and the corresponding IDCU 810-1, 810-2, 810-3, 810-4, 810-n can be setting up Ethernet communication and setting itself up as a server that can accept clients. Alternatively, the impact device 110-1, 110-2, 110-3, 110-n and the corresponding IDCU 810-1, 810-2, 810-3, 810-4, 810-n can be set up as clients. In an example implementation, the Ethernet initialization can be placed at the beginning of a code segment configured to implement an IDCU so that the initialization is compiled and placed in the first block of memory; otherwise the program can hang in an infinite loop. If for some reason the Ethernet initialization fails, a LED (e.g., a yellow LED) will flash (e.g., flash three times), and the microcontroller may reset itself and run the program from the beginning again. At the end of this phase, the red LED can turn off and another (e.g., green) LED will flash (e.g., flash three times) before all LEDs are turned off. In an example implementation, network information can be printed through the serial port. The network information can include the IP address, gateway, port, network mask, and the IP/port numbers for clients as they connect or disconnect.

In an example implementation, the Media Access Control (MAC) address of the hardware can be used to assign an IP address distinct from the devices connected to a network. Thus a unique Internet protocol (IP) address must be written into the code (for static IP), or the MAC address should be overwritten to make the IP address unique (e.g., for Dynamic Host Configuration Protocol).

After initializing the server, the IDCU 810-1, 810-2, 810-3, 810-4, 810-*n* and the impact device 110-1, 110-2, 110-3, 110-*n* initialize the hardware pertaining to sampling data. Sampling is set up so that the processor starts the sampling sequence. This is done by configuring several pieces of hardware to work together. For example, the ADCs, the FlexTime Module (FTM), the direct memory access module (DMA), and the programmable delay block (PDB) can operate together. Both ADCs are used so that both microphones can be sampled at the same time. The ADCs are configured to wait for a trigger from hardware (such as the PDB) and to average eight samples in order to give more accurate readings. The FTM is a multipurpose piece of hardware that, in this case, is used as a quadrature decoder. This automatically reads the quadrature signals from the angle encoder and increments/decrements a counter according to the number of ticks and phase of the two signals. The DMAs read from a source address and write to a destination address, which increments with each write. The DMAs are configured to read from ADC0, ADC1, and FTM (the quadrature decoder) in order to store the two microphone values and the angle. Lastly, the PDB is setup as a 100 kHz timer.

The sampling hardware can be set up as a chain reaction. The PDB generates three triggers simultaneously every 10 microseconds (us). Trigger 1 causes ADC0 to begin a conversion. When the conversion is complete, the ADCs conversion-complete flag triggers DMA0 to read the value and store it in an array. Similarly, trigger 2 causes ADC1 to begin a conversion, which triggers DMA1 to store the value upon completion. Trigger 3 causes DMA2 to store the current count of the FTM counter in an array. The FTM requires no trigger, as it constantly updates according to the signals from the angle encoder. After the DMAs have written half of the array, the DMA half-done flag is set, after which the processor begins transmitting the first half of the data. The sampling continues in parallel with the transmission until the second half of the data has been collected. At this time, the DMA done flag is set and the DMA interrupt-service routine is called. This routine disables the PDB, which stops the sampling chain reaction and tells the processor that the second half of the data is ready to be transmitted.

The impact device 110-1, 110-2, 110-3, 110-*n* waits for an external trigger before starting to sample. The mallet unit reads the Ethernet buffer waiting for the start command (with the distance stamp) from the distance unit. When the trigger is received from the distance unit, the impact device 110-1, 110-2, 110-3, 110-*n* rotates the cam initializing an impact, starts the PDB, and waits for the DMA half-done flag. After the flag, the mallet unit transmits the distance stamp and first half of the data and then waits for the DMA done flag, upon which the second half of the data is transmitted. The mallet unit then waits for the next command from the distance unit.

In an example implementation, an IDCU can be coded on a computing device that can be written in a command shell (e.g., iPython). An object for each impact device 110-1, 110-2, 110-3, 110-*n* can be used, each identical except for the IP address to which they connect. In an example implementation, there are seven impact devices. Therefore, there can be seven objects. Each object reads the buffer waiting to receive data from the mallet with the IP address. The object first receives the distance stamp and opens a file using the distance stamp as the name. Then the object reads all of the data and stores it in the file. The object then resumes waiting. Communication to the impact device 110-1, 110-2, 110-3, 110-*n* can be done serially (e.g., one after the other), and the order of communication can be fixed. Alternatively, communication to the impact device 110-1, 110-2, 110-3, 110-*n* can be done in parallel with no set order or as needed.

The components of the system can be mounted in a trailer for an example use scenario. For example, the components mentioned above can be mounted together to an aluminum plate and treated as one mallet unit and mounted to a custom trailer to complete the array of scanning mallets. The trailer can be configured to take multiple configurations. For example, the trailer can be configured in a travel configuration where portions of the trailer are collapsed raised/elevated/folded/packed up for travel. For example, the trailer can be in a test configuration where the trailer is expanded to cover a roadway. Changes to the configuration may be made manually, with a winch, with a hydraulic pulley system, and/or the like. The trailer may include devices to warn or direct traffic. For example, the trailer may include a traffic arrow to direct traffic around the trailer. For example, the trailer may include a sign or barrier used to warn other traffic.

Figure 9A:
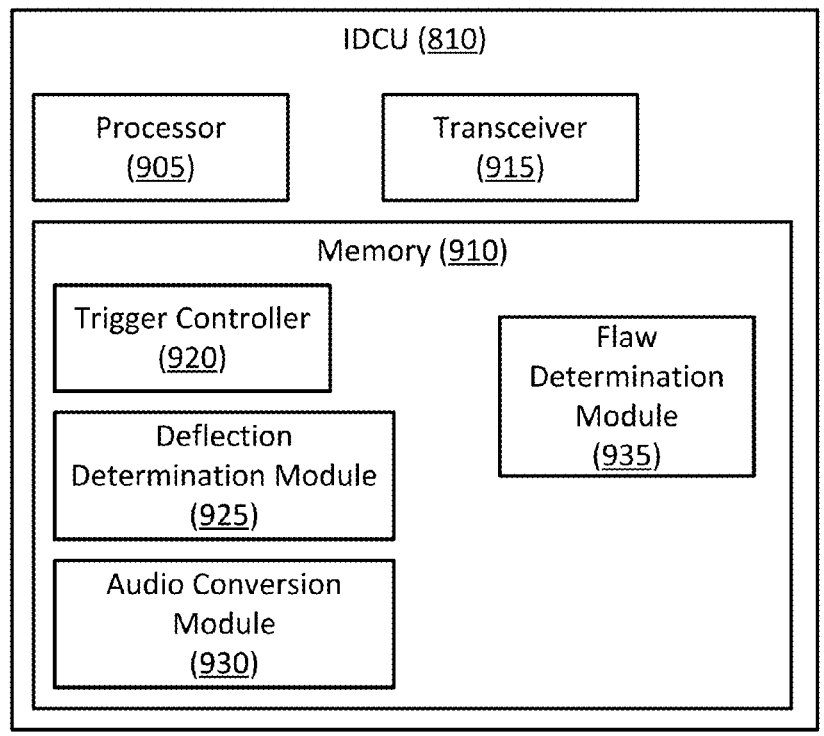

FIG. 9A is a block illustrating an IDCU 810 according to at least one example embodiment. As shown in FIG. 9A, the IDCU 810 includes a processor 905, a memory 910, and a transceiver 915. The memory 910 further includes a trigger controller 920, a deflection determination module 925, an audio conversion module 930, and a delamination determination module 935. The transceiver 915 can be configured to communicate with at least one other IDCU 810, controller 210, and/or other control device communicatively coupled with controller 105. The transceiver 915 can be configured to communicate using a wired and/or wireless signal using a wired and/or wireless protocol.

The trigger controller 920 can be configured to determine a timing at which an impact device 205 should initiate an impact test. The determination can be based on a user input. For example, a user (e.g., test technician) can generate a table including times (e.g., time increments) at which a particular IDCU should trigger an impact test. The motor control 920 can then read the table and determine the time for a corresponding impact device 205. For example, a user (e.g., test technician) can use a graphical user interface and enter a time span (e.g., 0.5 second, 1 second, and the like) between triggers. From the time span, the trigger controller 920 can determine a time span for the corresponding impact device 205. For example, if the corresponding impact device is the fifth out of seven impact devices 205 and the time span is 1 second, a first trigger can be at 5 seconds from the start of the test and every 7 seconds thereafter. Other timing trigger determinations may also be employed.

The deflection determination module 925 can be configured to determine a bounce back or rebound distance of the shaft 315 and/or knob 320 based on a signal from the controller 210. For example, during a calibration process, a lookup table can be generated that includes a digital (oct or hex) value and a distance value. The deflection determination module 925 can receive a signal from the controller 210. The signal can include the digital value, which can be used to look up the corresponding distance in the lookup table.

The audio conversion module 930 can be configured to determine a frequency response of an impact based on a signal from the controller 210. For example, during a calibration process, a lookup table can be generated that includes a frequency and a digital (oct or hex) value corresponding to a power (decibels) value for that frequency. The power value can be generated based on a calibration procedure for a type of material associated with the surface. The audio conversion module 930 can receive a signal from the controller 210. The signal can include the digital value, which can be used to look up the corresponding distance in the lookup table.

The flaw determination module 935 may be configured to determine whether a defect (e.g., a delamination defect) exists (or likely exists) in the surface and/or subsurface. The flaw determination module 935 may determine that a defect exists based on the measurements (e.g., acoustic wave measurements). Accordingly, the flaw determination module 935 may be configured to read the measurements stored in the raw data datastore 825. Then the flaw determination module 845 may determine associations between acoustic wave measurements, object impact times, and impact locations (e.g., GPS positions).

Figure 9B:
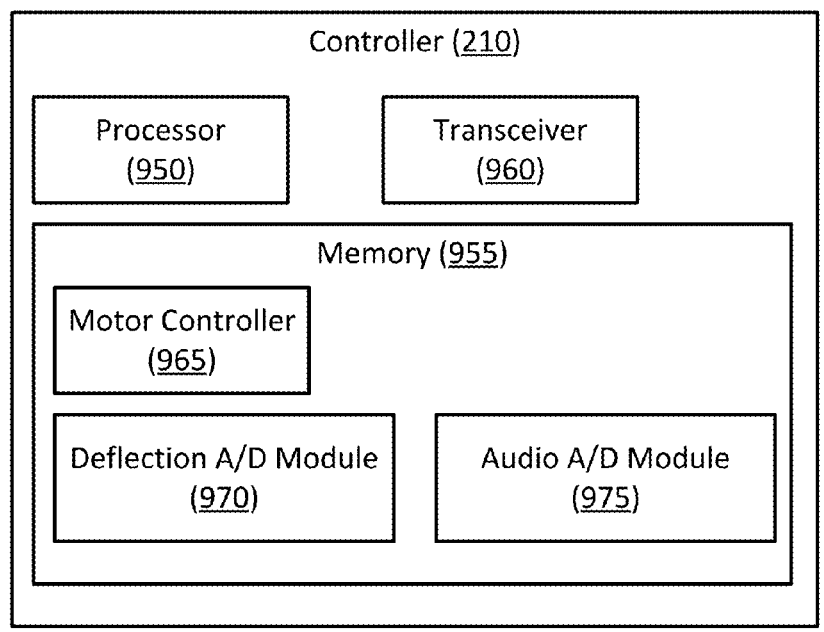

FIG. 9B is a block illustrating controller 210 according to at least one example embodiment. As shown in FIG. 9B, the controller 210 includes a processor 950, a memory 955, and a transceiver 960. The memory 955 further includes a motor control 965, a deflection analog-to-digital module 970, and an audio analog-to-digital module 975. The transceiver 960 can be configured to communicate with a corresponding IDCU 810, controller 105, at least one other controller 210, and/or other control device communicatively coupled with controller 210. The transceiver 960 can be configured to communicate using a wired and/or wireless signal using a wired and/or wireless protocol.

The motor controller 965 can be configured to communicate drive signals to the motor 215 based on timing signals received from the trigger controller 920. For example, when the trigger controller 920 communicates a trigger to initiate an impact, the motor controller 965 can drive the motor 215, causing the cam 305 to rotate and release shaft 315, which initiates an impact event. The deflection analog-to-digital module 970 converts a signal received from the angle encoder 225 into a digital code that can be communicated to the IDCU 810 via transceivers 915 and 960. The audio analog-to-digital module 975 converts a signal received from the microphone 230 into a digital code that can be communicated to the IDCU 810 via transceivers 915 and 960.

The elements shown in FIGS. 8, 9A, and 9B can be combined or included in different components of the overall system. For example, one or more of the raw data datastore 825, the filter module 830, the flaw determination module 845, and the flaw location module 850 can be included in the controller 210.

As discussed, example embodiments include a system that can locate flaws, defects, delaminations, and/or the like on surfaces such as roadways, parking lots, parking garages, bridges, buildings, dams, and/or the like. The system can further evaluate the surface for non-uniformities or discontinuities. The system can measure changes in stiffness of the surface (e.g., a pavement layer) along a road. As another example, the system can be configured to detect embedded objects (e.g., that should be below the surface). In an example implementation, the system can be deployed on a moving platform.

The described examples may be associated with bridges and pavements. However, example embodiments are not limited thereto. For example, applications can extend beyond testing of highway infrastructure. In an example embodiment, impedance and/or impact-echo technologies may be used for detecting areas of concern on a concrete bridge deck. The devices can be deployed (e.g., on a moving platform), and one or more maps can be produced that include spatial variations in properties of interest. In at least one example implementation, the maps may be sufficient, by themselves, for addressing the particular question that led to the testing. However, in another example implementation, the maps can be used as guides for additional work, such as completing repairs on a bridge deck. In other words, the map(s) may indicate areas of defective concrete that warrant removal and replacement. Further, a person (e.g., a contractor) may refer to the map(s) as he or she manually marks out the deck in a separate task. Manually marking the deck typically requires establishing a similar distance-measurement scheme on the bridge deck as used on the map and then manually identifying and marking the locations of interest on the deck surface. For example, the map(s) may be overlaid onto other survey maps in order to correlate test results with other visually identifiable features.

In another example, the impact-echo technology may be used for detecting areas of low (or relatively low as compared to surrounding regions) stiffness on a compacted layer of crushed stone or a layer of asphalt. From a map showing spatial variation in stiffness, the tested area could be manually marked, and the markings could then serve as guides for the engineers responsible for physical testing of the pavement layers. The engineer could then direct destructive (e.g., coring) or non-destructive testing of the marked areas to further investigate material properties of the pavement layers in those areas.

Manually marking a deck or pavement layer can be time-consuming. Accordingly, eliminating manual marking may be desirable. In an example implementation, the moving test platform can be configured to perform automatic marking. For example, at least one trigger criterion (e.g., a threshold value for a spatial variation) can be established that causes automatic marking should the trigger criterion be satisfied (e.g., met). Marking could be performed using the moving test platform configured to perform automatic marking during the original testing. For example, the marking apparatus could be mounted behind a data collection apparatus (e.g., mounted on the moving test platform). As such, the collected data may be evaluated and the automatic marking apparatus triggered based on the trigger criterion before the moving test platform moves beyond the location from which the data are collected.

Figure 10A:
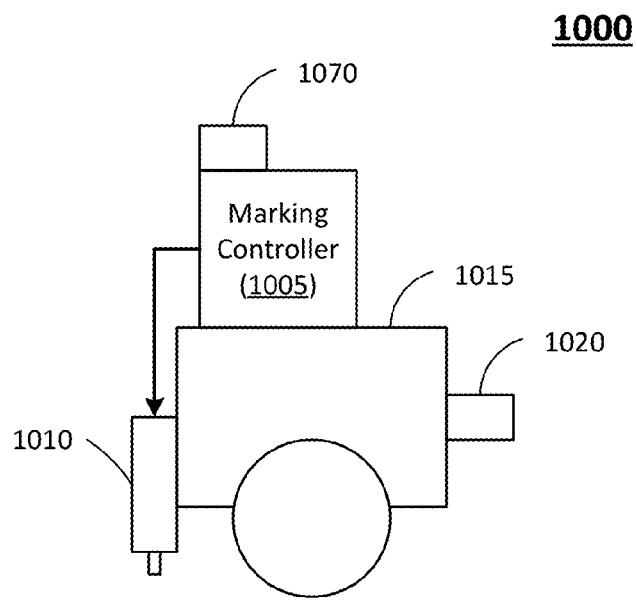
FIG. 10A illustrates a block diagram of a surface marking system according to at least one example embodiment.

FIG. 10A illustrates a block diagram of a marking system according to at least one example embodiment. As shown in FIG. 10A, the marking system 1000 includes a marking controller 1005, a marking apparatus 1010, a platform 1015, and a coupling mechanism 1020. The coupling mechanism 1020 (e.g., a hitch) can be coupled with a vehicle (not shown). Therefore, the platform 1015 can be a moving platform under propulsion of a vehicle.

Figure 10B:
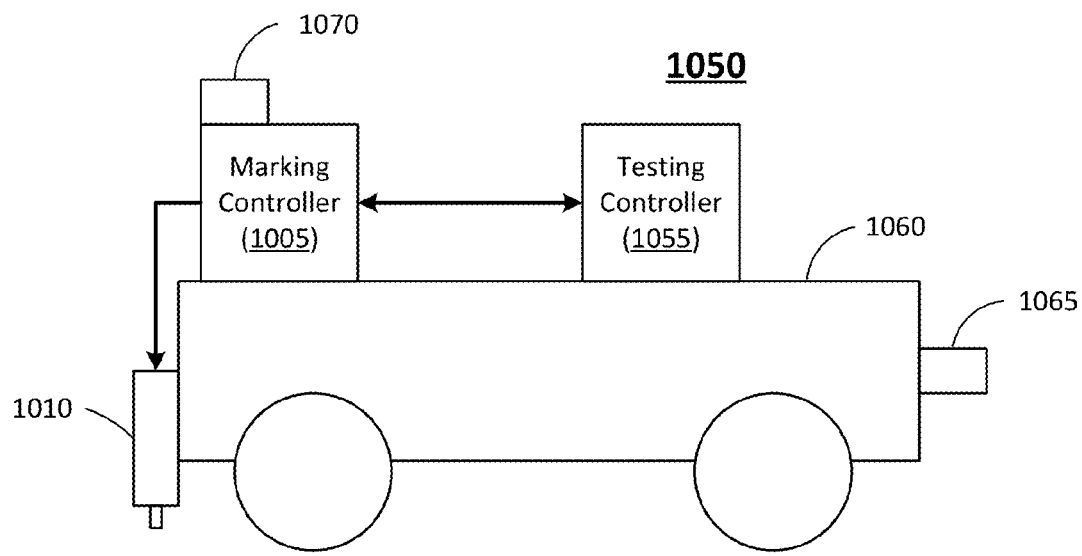
FIG. 10B illustrates a block diagram of another surface marking system according to at least one example embodiment.

FIG. 10B illustrates a block diagram of another surface marking system according to at least one example embodiment. As shown in FIG. 10B, the surface marking system 1050 includes the marking controller 1005, the marking apparatus 1010, a platform 1060, and a hitch 1065. The surface marking system 1050 further includes a testing controller 1055, which can be an element of a larger non-destructive testing system. Each of the elements shown in FIGS. 10A and 10B can be combined on and/or in association with one or more vehicles. The vehicles can be motorized or un-motorized. An un-motorized vehicle can be pulled and/or pushed by a motorized vehicle, an operator, etc.

In one or more example implementations, the testing device can be equipped with a data processing module (e.g., as an element of the testing controller 1055) configured to evaluate incoming test data and compare the test data to a trigger criterion or set of trigger criteria. The data processing module can signal (e.g., cause a signal to be transmitted) to the marking system 1000 at a location from which the test data were collected upon determining that the data meets the criterion or criteria (e.g., exceeds, matches, or is less than a threshold value(s)). For example, the testing controller 1055 can include a processing module configured to cause (e.g., trigger) the testing controller to signal the marking apparatus 1010 to mark a defect on a tested pavement should the tested pavement include a defect (e.g., based on the trigger criterion or criteria).

Accuracy in the automatic marking system could be ensured, for example, through an automatic location tracking feature (e.g., as an element of the marking controller 1005) on the moving platform and knowledge of the relative locations of the data collection apparatus and the marking apparatus on the test device. The automatic location tracking feature could incorporate a distance measurement instrument, a global positioning system, and/or another similar system.

In an example implementation, the marking apparatus 1010 can be (or include) an electrically activated mechanical system for spraying paint. For example, the paint can be in a standard upside-down spray can commonly used for utility marking. Alternatively, the paint can be in a different kind of container and/or dispensed in a fashion other than spraying (writing with a paint pen, launching paintball markers, etc.). A marking material other than paint can also be used (e.g., ink, dye, chalk, and/or the like).

In some implementations, a marker (e.g., paint or other marking material) may have special characteristics including being electrically conductive, magnetic, washable, visible only in certain conditions (e.g., when viewed under infrared or fluorescent light), and/or so forth. In other words, using a paint with special characteristics can include making the paint invisible under natural conditions, which may ensure that drivers (e.g., on a bridge or roadway) would not be confused by the additional markings.

In some implementations, multiple markers (e.g., paint), colors, patterns, and/or intensities can be utilized. For example, each color, pattern, and/or intensity could correspond to a particular trigger criterion. Accordingly, multiple levels of a given property and/or multiple types of properties could be indicated on a surface. The multiple levels of a given property and/or multiple types of properties could be marked on a surface simultaneously for devices that have the ability to simultaneously (or non-simultaneously) make such measurements. In addition, the marking system 1000 and/or 1050 could be configured to mark a center or middle of an area of interest (e.g., concern) or to mark an edge or boundary of an area of interest.

Example implementations can include indicating geospatial position of the testing equipment during testing. The on-board automatic marker can apply a mark (dot, dots, short line, and the like.) in, for example, a grid or similar layout, that can be photographed by a GPS-equipped on-board camera 1070 during testing so that a determination can be made as to where a test was performed after leaving the test lane, site, etc. The mark location would be at a known position relative to the testing apparatus, and the pictures, once stitched together to create a single image (using the GPS coordinates and image analysis techniques), would then indicate the exact path of testing down the bridge deck, pavement, and the like. In an example implementation, the camera can be programmed to take many overlapping pictures of the test site during testing.

A map of the measurements could then be overlaid directly onto the stitched image and used for analysis, review, and the like. If the marks were relatively stable (e.g., still visible after some elapsed time), the marks would serve as physical reference points on the tested surface that would enable a contractor, for example, to easily locate defects and/or discontinuities. In other words, the marks would provide a physical relationship between the map and the tested surface that would enable the contractor to readily locate defects on the surface that are marked on the map.

In some implementations, marks can be applied on both edges of the tested path (along the outer channels of the testing apparatus), which will also serve the purpose of helping the driver of the tow vehicle (or operator pulling or pushing a non-motorized trailer, cart, etc.) visually see where he or she has already tested during the testing process, prior to the development of any maps at all. The apparatus could be programmed to apply a mark(s) every so many feet down the road (e.g., every 6 or 12 ft) and may involve the use of different colors, patterns, intensities, and/or types of marking. In other implementations, marks may be applied on just one side, in the middle, or in other locations relative to the test path, as desired.

Figure 11:
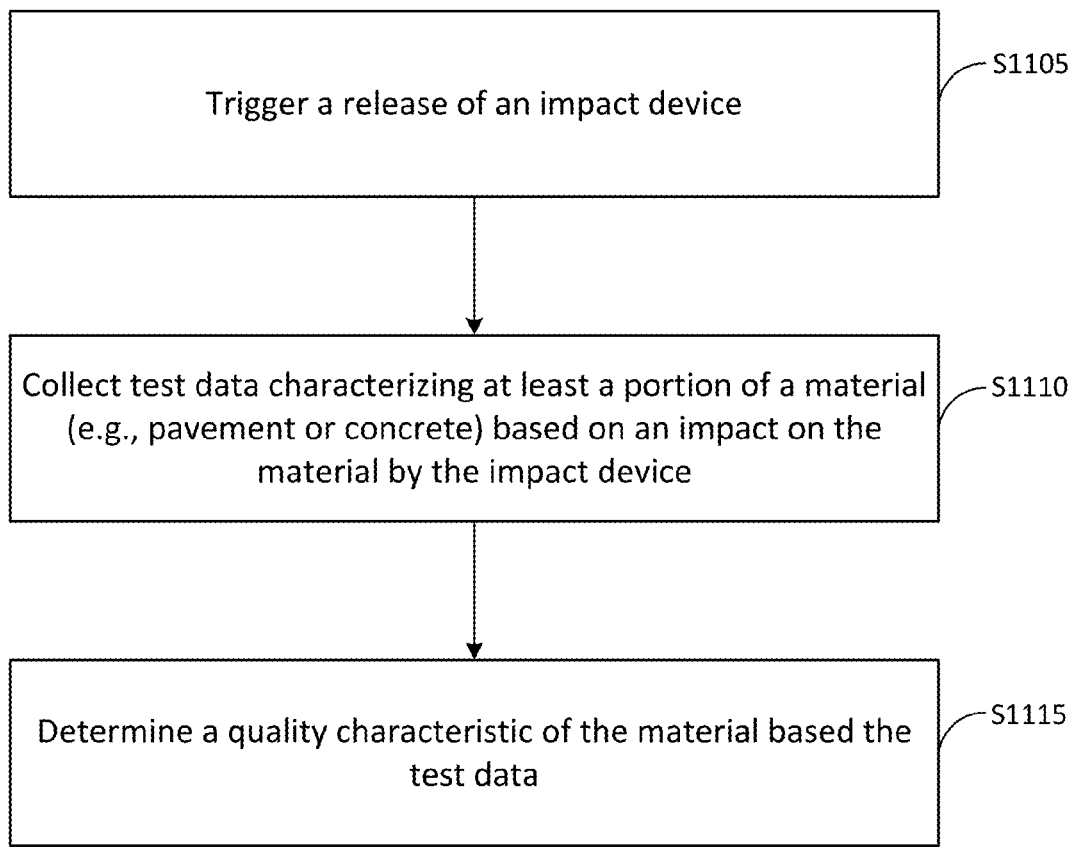
FIG. 11 illustrates a method of operating a non-destructive test system according to at least one example embodiment.
Figure 12:
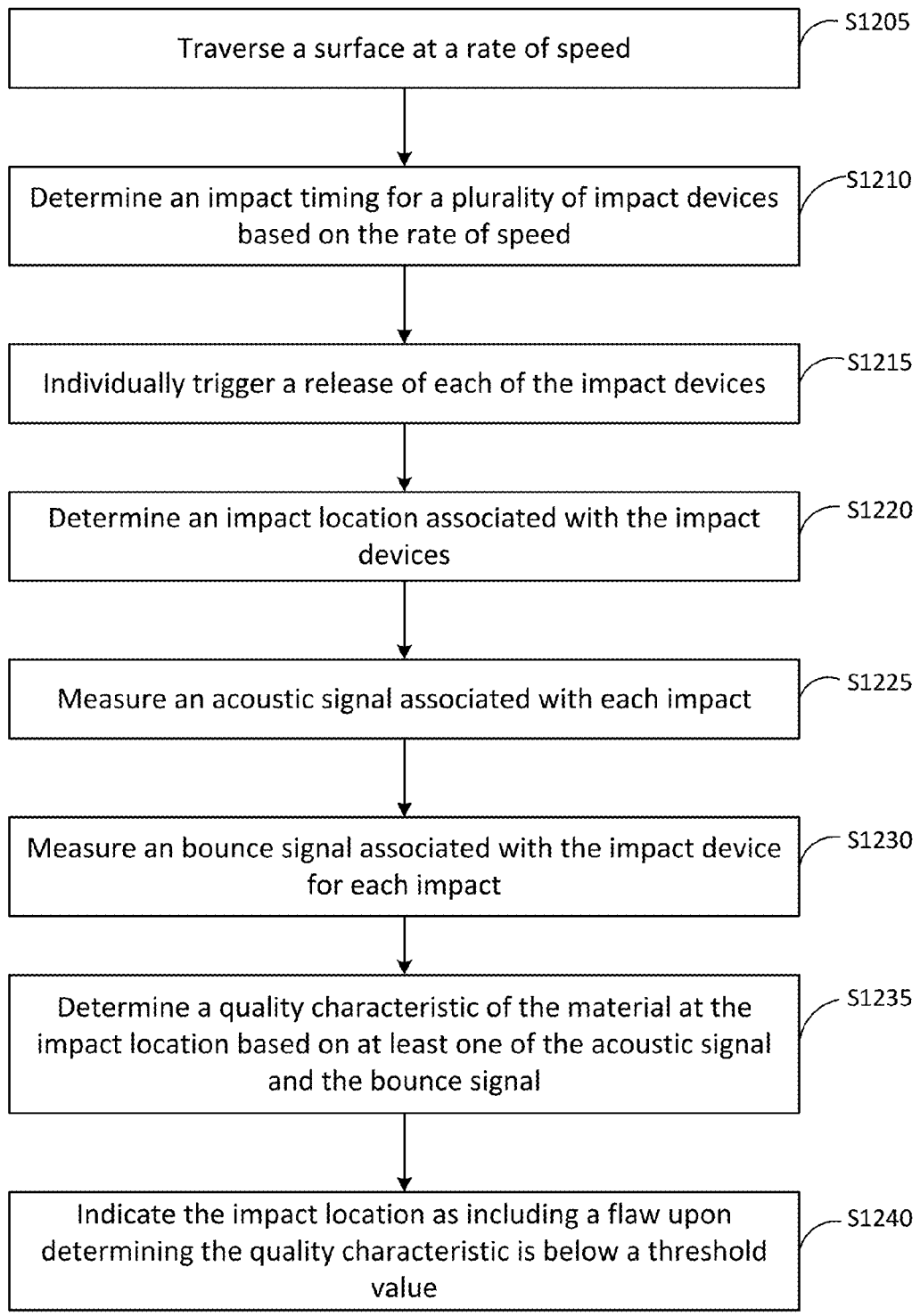
FIG. 12 illustrates another method of operating a non-destructive test system according to at least one example embodiment.
Figure 13:
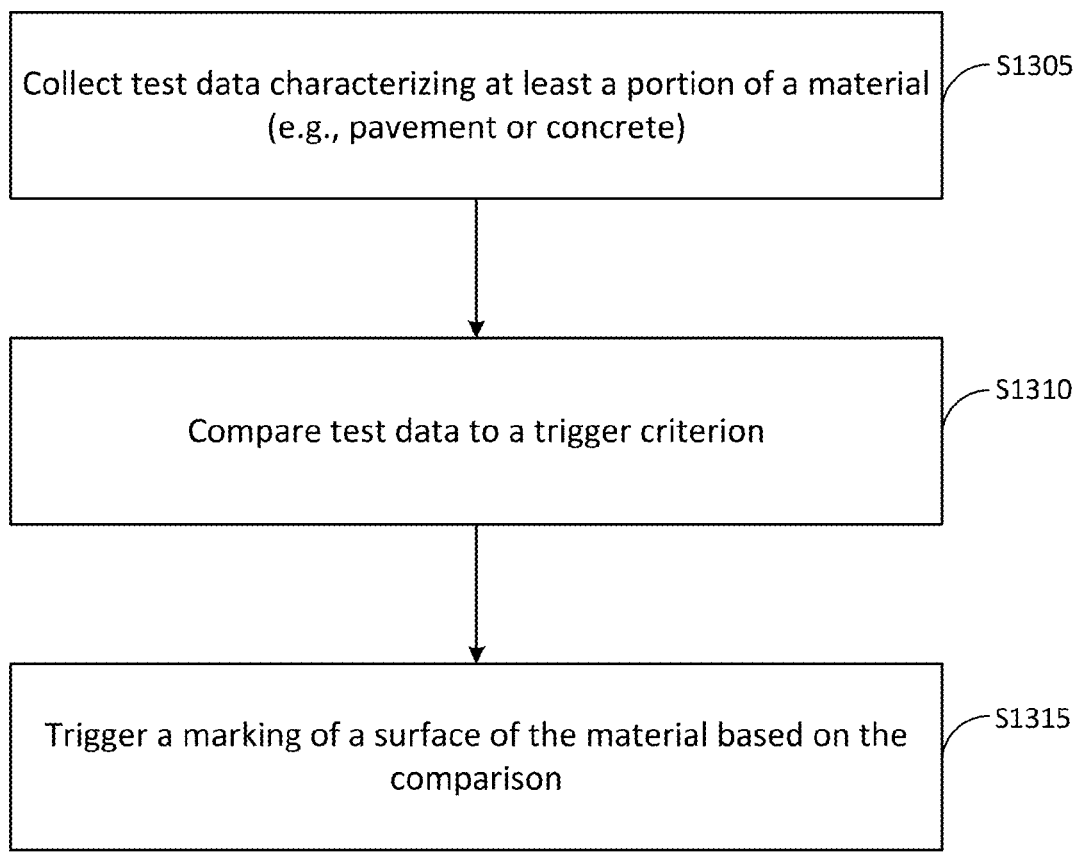
FIG. 13 illustrates a method of operating a surface marking system according to at least one example embodiment.

FIGS. 11-13 illustrate flowcharts for detecting and/or marking a defect in a surface according to at least one example embodiment. The steps described with regard to FIGS. 11-13 may be performed due to the execution of software code stored in a memory associated with an apparatus (e.g., as shown above) and executed by at least one processor associated with the apparatus. However, alternative embodiments are contemplated such as a system embodied as a special-purpose processor. Although the steps described below are described as being executed by a processor, the steps are not necessarily executed by a same processor. In other words, at least one processor may execute the steps described below with regard to FIGS. 11-13.

FIG. 11 illustrates a method of operating a non-destructive test system according to at least one example embodiment. As shown in FIG. 11, in step S1105 a release of an impact device can be triggered. For example, an IDCU for a corresponding impact device may trigger the release at a determined time and/or distance. The trigger may include communicating a signal to the impact device. The signal may cause a motor controller associated with the impact device to apply, for example, a voltage to a motor, causing the motor to turn a cam that releases a shaft that facilitates an impact on the tested surface by a knob attached to the shaft.

In step S1110 test data characterizing at least a portion of a material (e.g., pavement or concrete) can be collected based on an impact on the material by the impact device. For example, the knob impacts the surface of the material, causing acoustic signals (e.g., an echo) to be generated and the knob to rebound away from the surface. Data associated with the acoustic signals (e.g., frequency response data) and with the rebound (e.g., distance data) can be collected. In an example implementation, the frequency response and the height of the rebound can indicate whether or not there is a defect, discontinuity, etc. in the material at the tested location.

In step S1115 a quality characteristic of the material can be determined based on the test data. For example, the frequency response data and the distance data can be compared to a threshold value. If the frequency response data includes low frequency responses above the threshold value (e.g., a power of the low frequency response) and/or the rebound is below a threshold height, a flaw can exist in the material. The quality characteristic can relate to a flaw (e.g., delamination), material discontinuity (e.g., a metal substance in subsurface concrete), and/or material property (e.g., stiffness).

FIG. 12 illustrates another method of operating a nondestructive test system according to at least one example embodiment. As shown in FIG. 12, in step S1205 a surface is traversed at a rate of speed. For example, a trailer including test equipment configured to perform a nondestructive test of a material (e.g., concrete on a bridge) is pulled/pushed across the surface.

In step S1210 an impact timing (or distance) for a plurality of impact devices can be determined based on the rate of speed. For example, an impact test may be desired every 8 inches along the surface of the bridge. Using the rate of speed, a time or time span to cause an impact for each impact device can be determined.

In step S1215 a release of each of the impact devices can be individually triggered. For example, an IDCU for a corresponding impact device may trigger the release at a determined time and/or distance. The trigger may include communicating a signal to the impact device. The signal may cause a motor controller associated with the impact device to apply, for example, a voltage to a motor, causing the motor to turn a cam that releases a shaft and facilitates an impact on the tested surface by a knob attached to the shaft. For example, if the corresponding impact device is the fifth out of seven impact devices and the time span is 1 second, a first trigger can be at 5 seconds from the start of the test and every 7 seconds thereafter.

In step S1220 an impact location associated with the impact devices can be determined. For example, the location may be a relative position based on a start position on a structure (e.g., a bridge). For example, the location may be a geo-position based on a signal received from a GPS device. As another example, the location may be determined from image analysis of photographs taken during testing. A location of a test may be determined through the use of two or more of these and/or other methods. An acoustic signal (S1225) associated with each impact and a bounce signal (S1230) associated with the impact device for each impact are determined as discussed above.

In step S1235 a quality characteristic of the material at the impact location can be determined based on at least one of the acoustic signal and the bounce signal. For example, the frequency response data and the distance data can be compared to a threshold value. If the frequency response data includes low frequency responses above the threshold value (e.g., a power of the low frequency response) and/or the rebound is below a threshold height, a flaw can exist in the material.

In step S1240 the impact location can be characterized as having a flaw upon determining whether the quality characteristic is above or below a threshold value, between threshold values, etc. For example, a marker may be indicated (e.g., painted) on the surface at the location. For example, the data representing the measurements and the flaw may be stored in relation to the location. For example, a map may be generated including indications of the flaw. The quality characteristic can relate to a flaw (e.g., delamination), material discontinuity (e.g., a metal substance in subsurface concrete), and/or material property (e.g., stiffness).

FIG. 13 illustrates a method of operating a surface marking system according to at least one example embodiment. As shown in step S1305, test data characterizing at least a portion of a material (e.g., pavement or concrete) can be collected. The test data can be collected using a nondestructive test method as described above. In step S1310 the test data can be compared to a trigger criterion (or condition). In step S1315 a marking of a surface of the material can be triggered based on the comparison.

For example, data can be compared to the trigger criteria (e.g., by the testing controller 1055) and may be collected by an apparatus mounted to the same moving platform to which the marking apparatus is mounted (e.g., as shown in FIG. 10B), or the data collection apparatus and marking apparatus can be on separate platforms (e.g., as partially shown in FIG. 10A). In the latter case, active communication between the two apparatuses could be provided through wired or wireless communication. In one example implementation, the apparatuses could be deployed on separate platforms with a time differential between a data evaluation process and a marking process; separating the two apparatuses may provide additional time for data evaluation before marking would occur.

Simultaneous data collection and marking may not be necessary or may not be desirable. Therefore, in an alternative embodiment, data collection can occur before marking. For example, data can be collected, and then (e.g., at a later time) the marking apparatus can rely on pre-prepared location-referenced data rather than active measurements (e.g., as shown in FIG. 10A). For example, this configuration may be appropriate when the data collection process moistens the tested surface to the point that marking the surface is difficult until after some drying occurs. For example, this configuration may be appropriate when trigger criteria cannot be developed until after the collected data are interpreted at the office. Being able to deploy the automatic marking system independent of other testing devices could then be advantageous because only the automatic marking system would need to be taken back to the deck or pavement for marking, and the data collection apparatus could be deployed elsewhere. In this case, the automatic marking system would have its own automatic location tracking feature (e.g., a distance measurement instrument, a global positioning system, or another similar system).

Figure 14A:
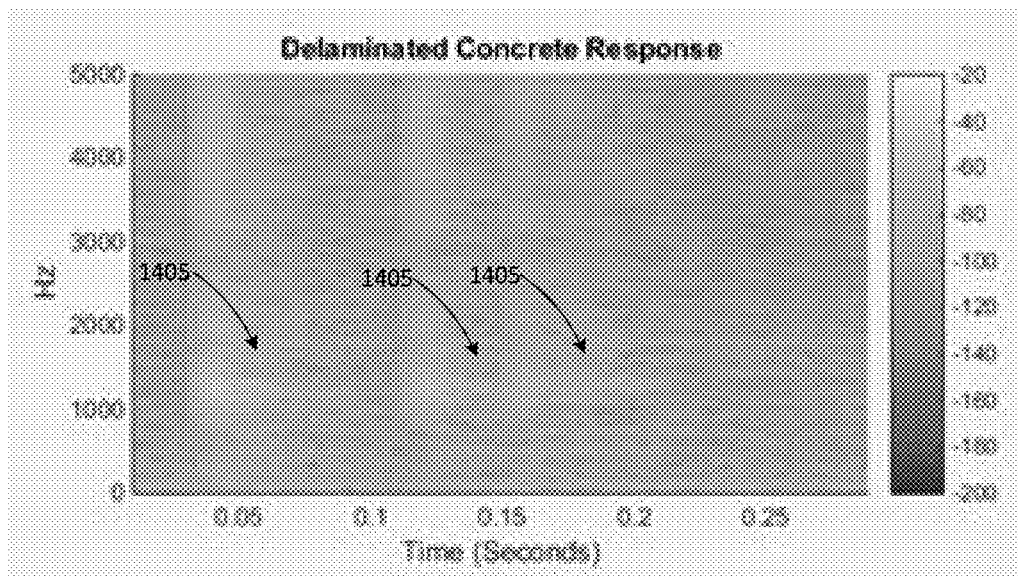
FIG. 14A illustrates a plot with an energy level indicating delamination according to at least one example embodiment.
Figure 14B:
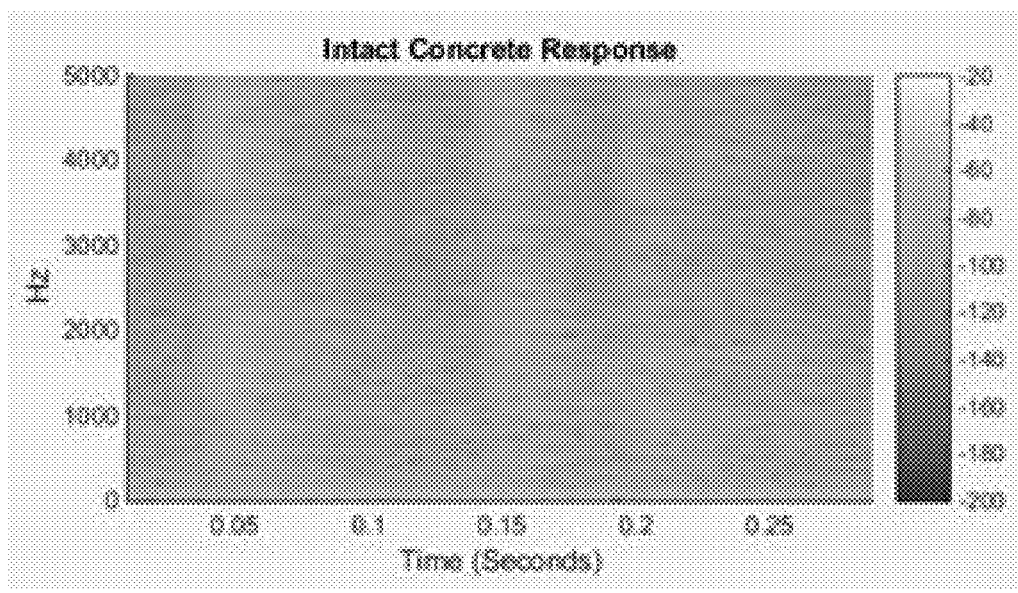
FIG. 14B illustrates a plot with an energy level indicating no delamination according to at least one example embodiment.

As example test output, FIGS. 14A and 14B illustrate some spectrograms that show the different frequency components that occur as different flexural modes are excited within the intact and delaminated concrete by each impact. The plot shown in FIG. 14A illustrates a higher low-frequency energy as compared to the plot shown in FIG. 14B for an intact location. The higher low-frequency energy shown in FIG. 14A illustrates a delamination 1405.

Figure 15:
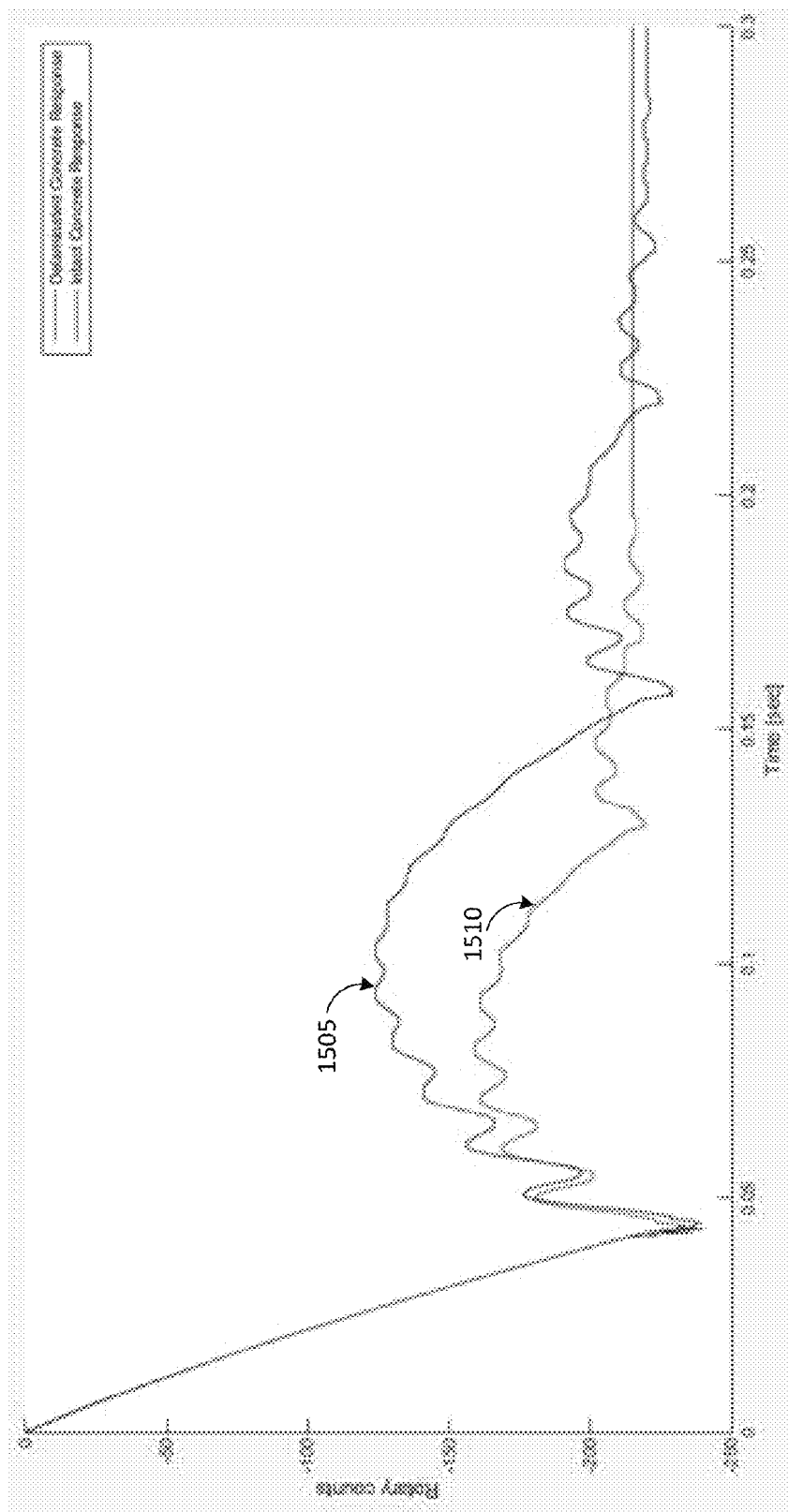
FIG. 15 illustrates a plot of two distinct impacts according to at least one example embodiment.

Example embodiments reveal defects, discontinuities, changes in stiffness, etc. by other mechanisms as well. Accordingly, an angle encoder can be attached to the fulcrum of the mallet to monitor the rebound and rotation of the shaft 315 after knob 320 strikes the material (e.g., concrete) surface. The surface and/or subsurface flaws create a different knob 320 rebound. FIG. 15 is a plot of two distinct impacts, one occurring over intact concrete (1510) and the other over delaminated concrete (1505). Each plot represents the mallet's position as it moved through its path of motion in striking the concrete. In both plots the initial drop towards the concrete surface, after the impact the mallet bounces back up, can be observed. Further, the intact concrete is shown to cause the knob 320 to rebound higher than the delaminated concrete. This is because the delaminated concrete allows more flexing, which in turn absorbs more of the impact, causing lower rebound.

Figure 16:
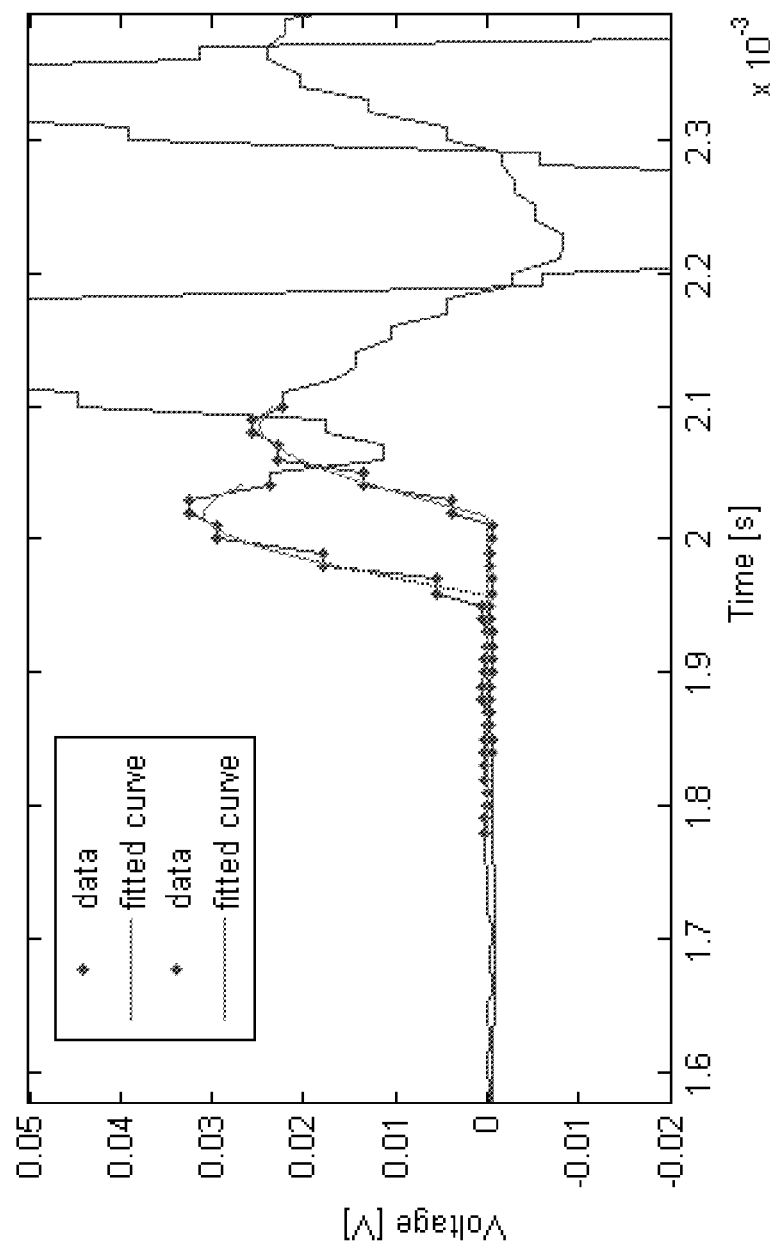
FIG. 16 illustrates a calculation of arrival times of two acoustic waves due to the impact according to at least one example embodiment.

An additional feature of having the microphones is the computation of the wave speed passing through the concrete. Thus, the wave speed can be directly calculated as shown in FIG. 16. For example, the wave speed through the intact concrete can be approximately 54% faster than through the delaminated concrete. The wave speed can be related to the effective Young's modulus of the material. FIG. 16 illustrates a calculation of arrivals of the two acoustic waves due to the impact. A parametric fit is performed on the data to find the start of a sinusoidal waveform. Then the start times of these sinusoidal fits are used to calculate the time difference of arrival. Knowing the distance between the microphones then allows calculation of the wave speed.

Figure 17A:
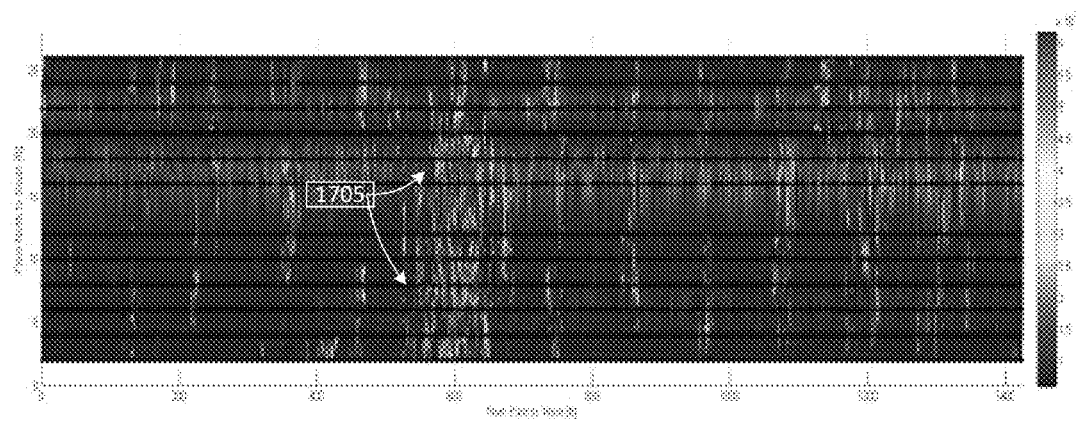
FIGS. 17A and 17B illustrate a plot representing points that need repair or replacement in a two-lane bridge. The areas indicated as 1705 show the points that need repair or replacement.

Example implementations using the microphone recordings (e.g., acoustic responses) and mallet angle measurements for each impact can distinguish between intact and deteriorated locations in the tested surface. In one implementation, a map based on microphone readings revealed delaminations on a tested concrete bridge deck surface. The map, shown in FIG. 17A, represents the actual length and width of a two-lane bridge. The areas indicated as 1705 are points that need repair or replacement.

After the map was generated, it was compared to a map generated using the chaining procedure. An explanation of chaining is given above, and the map generated for this same bridge by this process is shown in FIG. 17B.

Figure 17B:
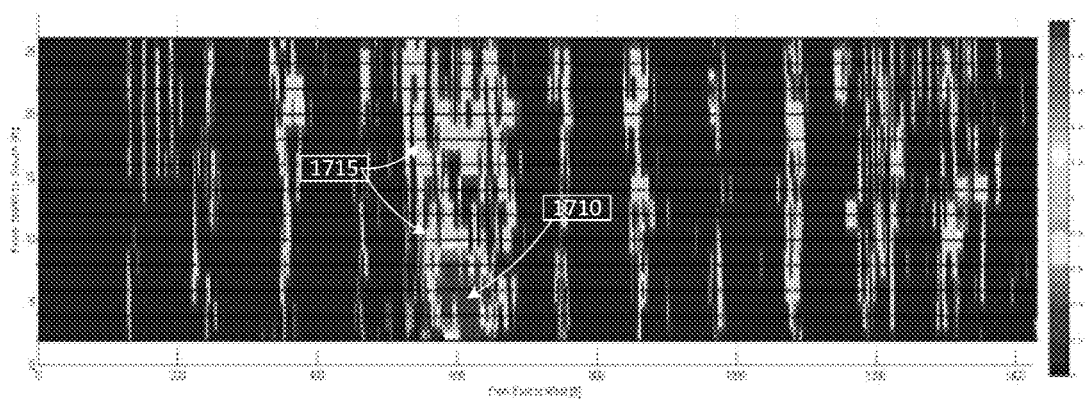

The color scheme used in FIG. 17B is slightly different than the one used in FIG. 17A. In FIG. 17B, areas indicated as 1710 are areas that have been patched already (e.g., no longer delaminated), and the areas indicated as 1715 indicate delaminations detected during acoustic testing (e.g., based on the microphone recordings). The delaminations found using the chaining procedure correspond with the delaminations found using the acoustic impact-echo process.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device. Various implementations of the systems and techniques described here can be realized as and/or generally be referred to herein as a circuit, a module, a block, or a system that can combine software and hardware aspects. For example, a module may include the functions/acts/computer program instructions executing on a processor (e.g., a processor formed on a silicon substrate, a GaAs substrate, and the like) or some other programmable data processing apparatus.

Some of the above example embodiments are described as processes or methods depicted as flowcharts. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Methods discussed above, some of which are illustrated by the flow charts, may be implemented by hardware, software, firmware, middleware, microcode, hardware description languages, or any combination thereof. When implemented in software, firmware, middleware or microcode, the program code or code segments to perform the necessary tasks may be stored in a machine or computer readable medium such as a storage medium. A processor(s) may perform the necessary tasks.

Specific structural and functional details disclosed herein are merely representative for purposes of describing example embodiments. Example embodiments, however, may be embodied in many alternate forms and should not be construed as limited to only the embodiments set forth herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments. As used herein, the term and/or includes any and all combinations of one or more of the associated listed items.

It will be understood that when an element is referred to as being connected or coupled to another element, it can be directly connected or coupled to the other element or intervening elements may be present. In contrast, when an element is referred to as being directly connected or directly coupled to another element, there are no intervening elements present. Other words used to describe the relationship between elements should be interpreted in a like fashion (e.g., between versus directly between, adjacent versus directly adjacent, etc.).

The terminology used herein is for the purpose of describing particular embodiments only and is not intended to be limiting of example embodiments. As used herein, the singular forms a, an and the are intended to include the plural forms as well, unless the context clearly indicates otherwise. It will be further understood that the terms comprises, comprising, includes and/or including, when used herein, specify the presence of stated features, integers, steps, operations, elements and/or components, but do not preclude the presence or addition of one or more other features, integers, steps, operations, elements, components and/or groups thereof.

It should also be noted that in some alternative implementations, the functions/acts noted may occur out of the order noted in the figures. For example, two figures shown in succession may in fact be executed concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Portions of the above example embodiments and corresponding detailed description are presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

In the above illustrative embodiments, reference to acts and symbolic representations of operations (e.g., in the form of flowcharts) that may be implemented as program modules or functional processes include routines, programs, objects, components, data structures, etc., that perform particular tasks or implement particular abstract data types and may be described and/or implemented using existing hardware at existing structural elements. Such existing hardware may include one or more Central Processing Units (CPUs), digital signal processors (DSPs), application-specific-integrated-circuits, field programmable gate arrays (FPGAs) computers or the like.

It should be borne in mind, however, that all of these and similar terms are to be associated with the appropriate physical quantities and are merely convenient labels applied to these quantities. Unless specifically stated otherwise, or as is apparent from the discussion, terms such as processing or computing or calculating or determining of displaying or the like, refer to the action and processes of a computer system, or similar electronic computing device, that manipulates and transforms data represented as physical, electronic quantities within the computer system's registers and memories into other data similarly represented as physical quantities within the computer system memories or registers or other such information storage, transmission or display devices.

Note also that the software implemented aspects of the example embodiments are typically encoded on some form of non-transitory program storage medium or implemented over some type of transmission medium. The program storage medium may be magnetic (e.g., a floppy disk or a hard drive) or optical (e.g., a compact disk read only memory, or CD ROM), and may be read only or random access. Similarly, the transmission medium may be twisted wire pairs, coaxial cable, optical fiber, or some other suitable transmission medium known to the art. The example embodiments not limited by these aspects of any given implementation.

Lastly, it should also be noted that whilst the accompanying claims set out particular combinations of features described herein, the scope of the present disclosure is not limited to the particular combinations hereafter claimed, but instead extends to encompass any combination of features or embodiments herein disclosed irrespective of whether or not that particular combination has been specifically enumerated in the accompanying claims at this time.

What is claimed is:

1. A non-destructive test system comprising:
    a plurality of impact devices including a knob configured to generate at least one flexural mode in a material when a surface of the material is impacted by the knob;
    a controller configured to independently control each of the plurality of impact devices, the controller having a communications channel for each of the plurality of impact devices; and
    a microphone configured to detect an acoustic response generated upon impact of the knob on the surface of the material, the acoustic response being based on the at least one flexural mode generated in the material, the acoustic response being in a direction normal to the surface of the material, the microphone not being in contact with the surface of the material.

2. The non-destructive test system of claim 1, further comprising an encoder configured to generate a signal based on a bounce of the knob off the surface after impact on the surface.

3. The non-destructive test system of claim 1, wherein
    the plurality of impact devices are attached to a trailer configured to traverse the surface,
    the plurality of impact devices are communicatively coupled to each other using an Ethernet protocol, and
    the plurality of impact devices are communicatively coupled to the controller using the Ethernet protocol, each of the plurality of impact devices having a different address.

4. The non-destructive test system of claim 1, wherein the controller is further configured to determine a characteristic at a location associated with the impact of the knob, the system further comprising:
    a marking device configured to mark the surface at the location of the characteristic.

5. The non-destructive test system of claim 1, further comprising:
    a marking device configured to mark the surface with a mark at an interval, to photograph the mark, to determine a location of the mark, and to associate the photograph with the location.

6. The non-destructive test system of claim 1, wherein
    the controller is further configured to determine a characteristic at a location associated with the impact of the knob, and
    the controller is further configured to generate a map indicating the location of the characteristic.

7. The non-destructive test system of claim 1, wherein
    the controller is further configured to determine a characteristic at a location associated with the impact of the knob, and
    determining the characteristic includes at least one of time domain filtering, frequency domain filtering, and signal separation of an acoustic wave detected by the microphone, wherein
    time domain filtering includes:
        band pass filtering using a window that passes acoustic waves representing the impact,
    frequency domain filtering includes:
        converting the acoustic wave into the frequency domain,
        determining a center frequency of a contour, and
        identifying a defect based on the center frequency of the contour and a threshold value, and
    signal separation includes:
        separating impact acoustic waves from noise using an eigenvalue analysis of a matrix-pencil.

8. The non-destructive test system of claim 1, wherein the microphone is a first microphone, the system further comprising:
    a second microphone configured to detect the acoustic response generated upon impact of the knob on the surface of the material, the acoustic response being based on the at least one flexural mode generated in the material, the controller is further configured to determine a characteristic at a location associated with the impact of the knob based on a time difference between detecting the acoustic response at the first microphone and detecting the acoustic response at the second microphone and a distance between the first microphone and the second microphone.

9. The non-destructive test system of claim 1, wherein the plurality of impact devices are attached to a trailer configured to traverse the surface, and the trailer is configured to be collapsed for transport between test sites.

10. A method comprising:
triggering a release of a first impact device of a plurality of impact devices by a controller;
triggering a release of a second impact device of the plurality of impact devices by the controller;
detecting, by a first microphone, at least one first acoustic wave associated with a first portion of a surface resulting from an impact by the first impact device, the first acoustic wave being in a direction normal to the first portion of the surface, the first microphone not being in contact with the first portion of the surface;
detecting at least one second acoustic wave associated with a second portion of a surface resulting from an impact by the second impact device;
identifying a first characteristic in the first portion of the surface based on the at least one first acoustic wave; and
identifying a second characteristic in the second portion of the surface based on the at least one second acoustic wave.

11. The method of claim 10, wherein the identifying of a first defect in the first portion of the surface includes at least one of time domain filtering, frequency domain filtering, and signal separation of an acoustic wave detected by the microphone, wherein
time domain filtering includes:
band pass filtering using a window that passes acoustic waves representing the impact,
frequency domain filtering includes:
converting the acoustic wave into the frequency domain,
determining a center frequency of a contour, and
identifying a defect based on the center frequency of the contour and a threshold value, and
signal separation includes:
separating impact acoustic waves from noise using an eigenvalue analysis of a matrix-pencil.

12. The method of claim 10, wherein the identifying of a second defect in the second portion of the surface includes at least one of time domain filtering, frequency domain filtering, and signal separation of an acoustic wave detected by the microphone, wherein
time domain filtering includes:
band pass filtering using a window that passes acoustic waves representing the impact,
frequency domain filtering includes:
converting the acoustic wave into the frequency domain,
determining a center frequency of a contour, and
identifying a defect based on the center frequency of the contour and a threshold value, and
signal separation includes:
separating impact acoustic waves from noise using an eigenvalue analysis of a matrix-pencil.

13. The method of claim 10, further comprising:
generating a first bounce signal based on a bounce off the first portion of a surface after impact associated with the first impact device on the first portion of a surface; and
generating a second bounce signal based on a bounce off the second portion of a surface after impact associated with the second impact device on the second portion of a surface, wherein
identifying the first characteristic in the first portion of the surface based on the first bounce signal, and
identifying the second characteristic in the second portion of the surface based on the second bounce signal.

14. The method of claim 10, further comprising:
marking the first portion of the surface at a location of the first characteristic; and
marking the second portion of the surface at a location of the second characteristic.

15. The method of claim 10, further comprising:
marking the surface with a mark at an interval;
photographing the mark;
determining a location of the mark; and
associating the photograph with the location.

16. The method of claim 10, wherein
detecting the at least one first acoustic wave reflected from the first portion of the surface resulting from the impact by the first impact device includes:
using the first microphone to detect a first of the at least one first acoustic wave, and
using a second microphone to detect a second of the at least one first acoustic wave, and
identifying the first characteristic in the first portion of the surface is based on a time difference between detecting the first of the at least one first acoustic wave at the first microphone and detecting the second of the at least one first acoustic wave at the second microphone and a distance between the first microphone and the second microphone.

17. The method of claim 10, wherein
the plurality of impact devices are attached to a trailer configured to traverse the surface, and
the trailer is configured to be collapsed for transport between test sites.

18. The method of claim 10, wherein triggering a release of a first impact device of a plurality of impact devices by a controller and triggering a release of a second impact device of the plurality of impact devices by the controller are based on determining a timing at which each of the plurality of impact devices are to initiate an impact test.

19. A non-destructive test system comprising:
a plurality of impact devices including a knob configured to generate at least one flexural mode in a material when a surface of the material is impacted by the knob;
a controller configured to independently control each of the plurality of impact devices, the controller having a communications channel for each of the plurality of impact devices;
a microphone configured to detect an acoustic response generated upon impact of the knob on the surface of the material, the acoustic response being in a direction normal to the surface of the material, the microphone not being in contact with the surface of the material; and
an encoder configured to generate a signal based on a bounce of the knob off the surface after impact on the surface.

20. The non-destructive test system of claim 19, wherein
the controller is further configured to determine a characteristic at a location associated with the impact of the knob, and
the controller is further configured to at least one of generate a map indicating the location of the characteristic and trigger a marking of the surface at the location of the characteristic.

\* \* \* \* \*